United States Patent [19]
Suzuki et al.

[11] Patent Number: 5,849,732
[45] Date of Patent: Dec. 15, 1998

[54] PHENOL COMPOUND HAVING ANTIOXIDATIVE ACTIVITY AND THE PROCESS FOR PREPARING THE SAME

[75] Inventors: Toshikazu Suzuki, Urawa; Hiroshi Ohmizu, Kyoto; Yoshimasa Hashimura, Urawa; Hitoshi Kubota, Hyogo-ken; Keiko Tanaka, Urawa, all of Japan

[73] Assignee: Tanabe Seiyaku Co., Ltd., Osaka, Japan

[21] Appl. No.: 800,680

[22] Filed: Feb. 14, 1997

[30] Foreign Application Priority Data

Feb. 15, 1996 [JP] Japan ................................ 8-028083
Nov. 12, 1996 [JP] Japan ................................ 8-300032

[51] Int. Cl.$^6$ .................. C07C 275/00; C07C 233/29; C07C 235/38; A61K 31/165; C07D 213/36; C07D 213/63; C07D 213/75; C07C 275/34

[52] U.S. Cl. .................. 514/212; 546/336; 546/337; 548/397.4; 560/21; 560/34; 560/169; 562/435; 564/27; 564/28; 564/50; 564/52; 564/56; 564/48; 514/237.8; 514/255; 514/307; 514/331; 514/332; 514/351; 514/357; 514/373; 514/406; 514/535; 514/539; 514/546; 514/587; 540/527; 544/120; 544/168; 544/360; 544/370; 546/146; 546/205; 546/247; 546/332

[58] Field of Search .................... 564/52, 48, 50, 564/27, 56, 28; 546/332, 336, 337, 247, 205, 146; 562/435; 544/382, 168, 120, 360, 370; 514/598, 587, 331, 357, 406, 237.8, 532, 307, 373, 255, 535, 212, 539, 546; 540/527; 548/379.4; 560/21, 34, 169

[56] References Cited

U.S. PATENT DOCUMENTS

| | | | |
|---|---|---|---|
| 2,867,659 | 1/1959 | Model et al. ......................... | 564/52 X |
| 3,689,550 | 9/1972 | Schellenbaum et al. ................ | 564/52 |
| 3,846,491 | 11/1974 | Mihaylov et al. .................... | 564/52 X |
| 4,460,602 | 7/1984 | Buckwalter et al. .................. | 424/322 |
| 5,063,247 | 11/1991 | Sekiya et al. ........................ | 574/585 |
| 5,290,814 | 3/1994 | Jackson et al. ....................... | 514/596 |
| 5,395,853 | 3/1995 | Jackson et al. ....................... | 514/596 |
| 5,426,022 | 6/1995 | Hagemann ............................ | 430/551 |

FOREIGN PATENT DOCUMENTS

| | | | |
|---|---|---|---|
| 0477778 | 9/1991 | European Pat. Off. . | |
| 0507291 | 10/1992 | European Pat. Off. . | |
| 0625507 | 11/1994 | European Pat. Off. . | |
| 0665216 | 8/1995 | European Pat. Off. . | |
| 1457172 | 9/1966 | France ..................................... | 564/50 |
| 1912553 | 10/1969 | Germany ................................ | 564/52 |
| 42-006174 | 3/1967 | Japan ....................................... | 564/52 |
| 94/22807 | 10/1994 | WIPO ..................................... | 564/52 |

OTHER PUBLICATIONS

Morel et al. (1984) *Arteriosclerosis* vol. 4, No. 4:357–364 (1984).

Kita et al. (1987) *Proc.Natl.Acad.Sci.USA*, vol. 84, pp. 5928–5931 (1987).

*Primary Examiner*—Floyd D. Higel
*Attorney, Agent, or Firm*—Birch, Stewart, Kolasch & Birch, LLP

[57] ABSTRACT

Disclosed are a phenol compound represented by the formula (1):

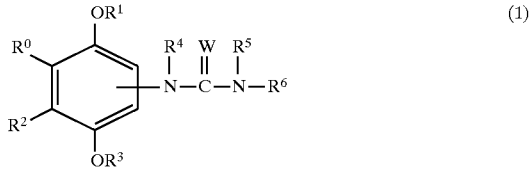

wherein $R^0$ represents H, alkyl or alkyloxy; $R^1$ represents alkyl; $R^2$ represents alkyl or alkyloxy; $OR^3$ represents OH; $R^4$ represents H, lower alkyl or acyl, each of the above substituents may be substituted; W represents O, S or $NR^7$; where $R^7$ represents H, alkyl, aryl, OH or alkyloxy, a group of the formula (2):

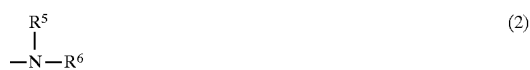

represents an amino which may be mono- or di-substituted or heterocyclic group containing N atom, or a pharmaceutically acceptable salt thereof, and a process for preparing the same.

19 Claims, No Drawings

PHENOL COMPOUND HAVING ANTIOXIDATIVE ACTIVITY AND THE PROCESS FOR PREPARING THE SAME

BACKGROUND OF THE INVENTION

This invention relates to a novel phenol compound and a process for preparing the same.

An increase of ischemic heart failure diseases caused by accumulation of cholesterol in an arterial wall such as atherosclerosis, cardiac infarction becomes social problems in the world.

As of today, medicines for decreasing the amount of blood cholesterol has been developed, but none of medicine which can reduce absorption of cholesterol in the small intestine or accumulation of cholesterol in the arterial wall, or which can reduce directly atherosclerosis itself has been found.

As an initial pathological change in atherosclerosis, accumulation of foam cells derived from monocytes/macrophages at the subendothelial space of an arterial wall is observed. Accumulation of lipid droplets into the foam cells occurs as follows 1) a low-density lipoprotein (LDL) in blood is chemically modified at the subendothelial space of an arterial wall and incorporated by monocytes/macrophages through scavenger receptors, 2) the incorporated modified LDL is hydrolyzed in lysosomes, and the formed free cholesterol is transferred to cytoplasm, 3) it is reesterified by acyl co-enzyme A cholesterol acyl transferase (ACAT) at the cytoplasm and accumulated as lipid droplets whereby foam cell formation, which leads to pathological change of atherosclerosis. Thus, by preventing the action of the ACAT, it is possible to prevent either the incorporation of cholesterol into a body or formation of cholesteryl esters.

As a compound having an activity of inhibiting ACAT, there may be described in, for example, Japanese Patent First Publications (Kokai) No. 188568/1990 and No. 92950/1993. However, the compounds described in the above references have ACAT inhibiting action but no effect on oxidative modification of LDL which plays an important role in the foam cell formation of macrophages in the development of atherosclerosis.

The foam cells which play an important role in the formation of atherosclerosis are derived from macrophages as the result of taking oxidatively modified LDL in the macrophages. Thus, the fact that the LDL which is oxidatively modified causes foam cell formation of macrophages and plays an important role in the development of the atherosclerosis has been reported by Morel et al. (see ARTERIOSCLEROSIS, vol. 4, pp. 357–364, 1984). Also, it has been clarified by the report of TORU KITA et al. (Proc. Natl. Acad. Sci. U.S.A., vol. 84, pp. 5928–5931, 1987) that the prevention of oxidative modification of LDL leads to the reduction of atherosclerosis. Accordingly, in addition to preventing ACAT as mentioned above, it is extremely important to inhibit oxidative modification of the LDL for preventing formation, development, and reduction of atherosclerosis.

It has not yet been completely clarified how the peroxidation reaction of lipids causes damage to cell membranes and finally cell death, but it has been understood as a common recognition that production and accumulation of active oxygen plays an important role in cell damage. Further, it is well-known that an active oxygen causes not only peroxidation of lipids but also modification of an enzyme or a protein and damage of a nucleic acid, and these results induce various organ failures. For example, in the heart, at an initial stage of myocardial infarction caused by coronary occlusion, a patient falls into critical condition such as cardiogenic shock or lethal arrhythmia so that a reperfusion treatment (deformation of thrombus, percutaneous transluminal coronary angioplasty (PTCA) or coronary artery bypass graft (CABG), etc.) for resuming blood flow is carried out as an initial treatment. However, in recent years, so-called ischemia/reperfusion injury in which cardiac muscle tissue is damaged by resuming blood flow has been noticed. It has been reported as a problem that an active oxygen participates in the phenomenon as one of the factors, and that oxygen radicals generated at the reperfusion cause reperfusion arrhythmia whereby cardiac muscle dysfunction is brought about by cell injury accompanied by decrease of ATP production or cell membrane destruction accompanied by increase of enzyme activities.

SUMMARY OF THE INVENTION

The present invention provides a novel phenol derivative having an antioxidative action which is effective for controlling atherosclerosis, cardiac infarction, cell damage and arrhythmia at ischemia/reperfusion by scavenging an active oxygen. Also, the present invention provides a process for preparing such a novel phenol derivative.

In order to solve the above problems, the present inventors by an exhaustive research have found that a novel phenol derivative controls development of atherosclerosis by inhibiting formation of foam cells of macrophage by an excellent anti-oxidative action and ACAT inhibiting action and controls myocardial infarction, cell damage and arrhythmia at ischemia/reperfusion by an excellent active oxygen scavenging action and anti-oxidative action, whereby the present invention.

That is, the present invention provides a phenol derivative represented by the formula (1):

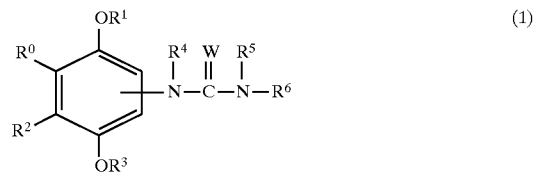

wherein $R^0$ represents hydrogen atom, an alkyl group which may be substituted or an alkyloxy group which may be substituted; $R^1$ represents an alkyl group which may be substituted; $R^2$ represents an alkyl group which may be substituted or an alkyloxy group which may be substituted; $OR^3$ represents a hydroxyl group which may be protected; $R^4$ represents hydrogen atom, a lower alkyl group or acyl group each of which may be substituted; W represents O, S or $NR^7$; wherein $R^7$ represents hydrogen atom, an alkyl group, an aryl group, hydroxyl group or an alkyloxy group, a group of the formula (2):

represents an amino group which may be mono- or di-substituted or a heterocyclic group containing nitrogen atom, or a pharmaceutically acceptable salt thereof.

Also, the present invention provides the process for preparing the above compound (1) or a pharmaceutically acceptable salt thereof according to the present invention comprising the steps of A) allowing a compound represented by the formula (c) or a reactive derivative thereof:

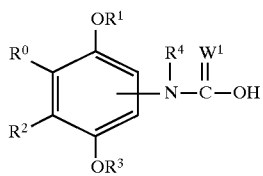 (c)

wherein $R^0$, $R^1$, $R^2$ and $R^4$ have the same meanings as defined above, $OR^{31}$ represents a hydroxyl group which may be protected; and $W^1$ represents O or S, to react with an amine compound represented by the formula (b):

 (b)

wherein $NR^5R^6$ represents an amino group which may be mono- or di-substituted or a heterocyclic group containing nitrogen atom, or a salt thereof to form a compound represented by the formula (1-a):

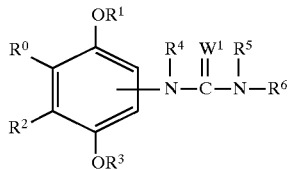 (1-a)

wherein the respective symbols have the same meanings as defined above; or

B) allowing an aniline compound represented by the formula (d):

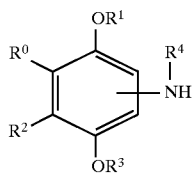 (d)

wherein the respective symbols have the same meanings as defined above, or a salt thereof to react with a reactive derivative of a carbamic acid compound represented by the formula (e):

 (e)

wherein the respective symbols have the same meanings as defined above, to form a compound represented by the formula (1-b):

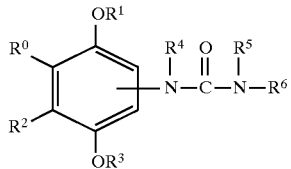 (1-b)

wherein the respective symbols have the same meanings as defined above; or

C) allowing the aniline compound represented by the above formula (d) to react with an isocyanate (or thioisocyanate) compound represented by the formula (f):

 (f)

wherein $R^{51}$ represents hydrogen atom, an alkyl group which may be substituted, an alkenyl group which may be substituted, an aryl group which may be substituted, an amino group which may be substituted or a heterocyclic group, and the other symbol has the same meaning as defined above, to form a compound represented by the formula (1-c):

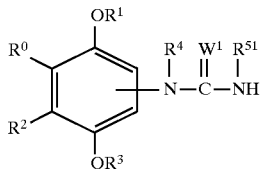 (1-c)

wherein the respective symbols have the same meanings as defined above; and, if necessary, D) when the group $W^1$ of the product represented by the formula (1-a) or (1-c) is sulfur atom, if desired, allowing the product (1-a) or (1-c) to react with an amine compound represented by the formula (g):

 (g)

wherein $R^7$ represents hydrogen atom, an alkyl group, an aryl group, hydroxyl group or an alkyloxy group, to form a compound of the formula (1-d):

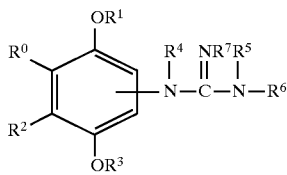 (1-d)

wherein the respective symbols have the same meanings as defined above, and

E) when the group $OR^{31}$ of the product is a protected hydroxyl group, removing the protecting group of said hydroxyl group, if desired, or when the group $OR^{31}$ of the product is hydroxyl group, if desired, after protecting the hydroxyl group, and converting the product to a pharmaceutically acceptable salt, if desired.

DESCRIPTION OF THE PREFERRED EMBODIMENTS

As the alkyl group, which may be substituted, represented by $R^0$ in the phenol derivative (1) of the present invention, there may be mentioned an alkyl group having 1 to 20 carbon atoms, and preferably a straight or branched lower alkyl group such as methyl group, ethyl group, isopropyl group or hexyl group, octyl group and hexadecyl group. As the alkyloxy group, which may be substituted, represented by $R^0$, there may be mentioned an alkyloxy group having 1 to 20 carbon atoms, and preferably a lower alkyloxy group such as methoxy group, octyloxy group and tetradecyloxy group, particularly methoxy group. As the $R^0$, hydrogen atom is particularly preferred.

As the alkyl group, which may be substituted, represented by $R^1$, there may be mentioned an alkyl group having 1 to 20 carbon atoms, preferably a straight or branched lower alkyl group such as methyl group, ethyl group, isopropyl group or hexyl group, octyl group and hexadecyl group, particularly preferably methyl group.

As the alkyl group, which may be substituted, represented by $R^2$, there may be mentioned an alkyl group having 1 to 20 carbon atoms, preferably a straight or branched lower alkyl group such as methyl group, ethyl group or tert-butyl group, octyl group, decyl group and tetradecyl group, particularly preferably a branched lower alkyl group such as tert-butyl group. Also, as the alkyloxy group, which may be substituted, represented by $R^2$, there may be mentioned an alkyloxy group having 1 to 20 carbon atoms, and preferably a lower alkyloxy group such as methoxy group, octyloxy group and tetradecyloxy group, particularly preferably methoxy group.

As the protecting group for the hydroxyl group, which may be protected, represented by $OR^3$, a conventional protecting group which can be a protecting group for hydroxyl group can be used, and there may be mentioned, for example, an acyl group, a lower alkyloxy-lower alkyl group, a lower alkyloxycarbonyl group, a lower alkylcarbonyloxy-lower alkyl group and an aralkyl group.

Also, when the hydroxyl group which may be protected is protected by an acyl group, as the said acyl group, there may be mentioned an aliphatic acyl group or an aromatic acyl group, and particularly preferably a lower alkylcarbonyl group or a lower cycloalkylcarbonyl group as the aliphatic acyl group.

Herein, the said acyl group may have a substituent, and there may be mentioned a group in which hydroxyl group is removed from a carboxyl group of an α-amino acid such as alanine, valine, glycine, aspartic acid, glutamic acid and lysine. The amino group of the group in which hydroxyl group is removed from a carboxyl group of an α-amino acid may be protected, and as the protecting group for the amino group, there may be mentioned, for example, an acyl group including a lower alkylcarbonyl group such as acetyl group and propionyl group, a lower alkyloxycarbonyl group, and a phenyl lower alkyloxycarbonyl group such as benzyloxycarbonyl group.

As a preferred example of the hydroxyl group, which may be protected, represented by $OR^3$, there may be mentioned hydroxyl group, a lower alkylcarbonyloxy-lower alkyloxy group (e.g., tert-butylcarbonyloxymethoxy group), an acyloxy group (e.g., a lower alkylcarbonyloxy group such as acetyloxy group and ethoxycarbonyloxy group, benzoyloxy group, glycyloxy group, alanyloxy group, valyloxy group, aspartyloxy group, glutamyloxy group and lysiloxy group), and particularly preferred is hydroxyl group.

Among the substituents represented by $R^4$, as the acyl group, there may be mentioned a lower alkylcarbonyl group such as acetyl group, and a group in which hydroxyl group is removed from a carboxyl group of an α-amino acid such as glycyl and alanyl, and as the alkyl group which may be substituted, there may be mentioned an alkyl group having 1 to 20 carbon atoms (e.g., a straight or branched lower alkyl group such as methyl group, ethyl group, isopropyl group or hexyl group, octyl group and hexadecyl group, particularly methyl group), and a heterocyclic group-substituted lower alkyl group (e.g., pyridylmethyl group), and as the $R^4$, hydrogen atom is preferred.

When W is represented by $NR^7$, the alkyl group in $R^7$ may include a lower alkyl group such as methyl group and ethyl group, the aryl group in $R^7$ may include phenyl group, the alkyloxy group in $R^7$ may include a lower alkyloxy group such as methoxy group and ethoxy group. As W, oxygen atom or sulfur atom is preferred and oxygen atom is particularly preferred.

As $R^5$ and $R^6$ when the group represented by the formula (2):

is an amino group which may be mono- or di-substituted, these may be the same or different and may be mentioned hydrogen atom, an alkyl group which may be substituted, an alkenyl group which may be substituted, an aryl group which may be substituted, an amino group which may be substituted and a heterocyclic group.

Among them, as the alkyl group which may be substituted, there may be mentioned an alkyl group, a halogenated alkyl group, a carboxyalkyl group, an alkyloxycarbonylalkyl group, a hydroxyalkyl group, a dihydroxyalkyl group, a trihydroxyalkyl group, an N-alkylaminoalkyl group, an N,N-dialkylaminoalkyl group, an N-(diphenylalkyl)aminoalkyl group, a carbamoylalkyl group, an N-alkylcarbamoylalkyl group, an N,N-dialkylcarbamoylalkyl group, an N-(dihydroxyalkyl)carbamoylalkyl group, a morpholinocarbonylalkyl group, a heterocyclic group-substituted alkyl group, a cycloalkyl group, a cycloalkylalkyl group, an arylalkyl group and a diarylalkyl group. As the alkenyl group which may be substituted, there may be mentioned an alkenyl group which have one or more double bonds and have 2 to 20 carbon atoms, preferably 2 to 8 carbon atoms, and those may be substituted by one or more alkyl groups.

As the amino group which may be substituted, there may be mentioned amino group, a monoalkylamino group, a dialkylamino group, an arylamino group, an arylsulfonylamino group and an arylcarbamoylamino group.

As the heterocyclic group and the heterocyclic group portion, there may be mentioned a saturated or unsaturated 3 to 12-membered monocyclic or dicyclic heterocyclic group containing a hetero atom(s) selected from sulfur atom, oxygen atom and nitrogen atom, and particularly preferred are those having 5 to 10-membered ring such as pyridyl group, pyridinio group, piperadinyl group, pyrrolidinyl group, morpholinyl group, pyradinyl group, piperidyl group, imidazolidinyl group, imidazolyl group, benzimidazolyl group, quinolyl group, tetrahydroquinolyl group and pyrazolinyl group. These heterocyclic groups may be, if necessary, mono-, di- or tri-substituted by 1 to 3 groups selected from hydroxyl group, a hydroxyalkyl group, an alkyloxy group, an alkyloxycarbonyl group, an alkylcarbonyl group, an alkyl group, a cycloalkyl group, a cycloalkylalkyl group, a pyridylalkyl group, oxo group, carboxyl group, phenyl group, a phenylalkyl group, a diphenylalkyl group, phenylpiperadinyl group, a phenylalkyloxycarbonyl group, an N-phenylcarbamoyl group and an N-phenylcarbamoylaminoalkyl group (the above-mentioned phenyl group or phenyl portion may be, if necessary, mono-, di- or tri-substituted by 1 to 3 substituents selected from a halogen atom, hydroxyl group, an alkyl group, an alkyloxy group, a dialkylaminoalkyloxy group, a cyano group, a dialkylamino group and trifluoromethyl group).

When the group represented by the formula (2):

is a nitrogen-containing heterocyclic group, that is, $R^5$ and $R^6$ are each bonded at their terminals to form a nitrogen-containing heterocyclic group with the adjacent nitrogen atom, said nitrogen-containing heterocyclic group may include a saturated or unsaturated 3 to 12-membered monocyclic or di-cyclic nitrogen-containing heterocyclic group which may further contain one or two hetero atoms selected from sulfur atom, oxygen atom and nitrogen atom in addition to the original nitrogen atom, and preferred are those having 5 to 10-membered ring. More specifically, there may be preferably mentioned, for example, piperazinyl group, piperidino group, piperidyl group, morpholino group, morpholinyl group, pyrrolidinyl group, thiomorpholinyl group, imidazolidinyl group, dihydroquinolyl group and tetrahydroquinolyl group. These nitrogen-containing heterocyclic group may be, if desired, mono-, di- or tri-substituted by 1 to 3 groups selected from the group consisting of a halogen atom, an alkyl group, hydroxyl group, a hydroxyalkyl group, an alkyloxy group, oxo group, carboxyl group, an alkyloxycarbonyl group, a phenylalkylaminoalkyl group, phenyl group, a halogenophenyl group, an aminophenyl group, a nitrophenyl group, an aminophenylalkenyl group, an aminoalkyl group, an aminophenylalkyl group, an N,N-diaminoalkylaminophenylalkyl group, an N-arylureidoalkyl group, a morpholinylphenylalkyl group, a pyridylalkyl group, a benzimidazolylalkyl group, a hydroxyphenyl group, a diaminophenyl group, an N-alkylaminophenyl group, an N,N-dialkylaminophenyl group, an amidinophenyl group, a piperadinophenyl group, a morpholinophenyl group, pyrrolidinyl group, piperidyl group, indolyl group, pyrimidinyl group, benzimidazolyl group and pyridyl group.

As the above-mentioned cycloalkyl group and the cycloalkyl portion, there may be mentioned a cycloalkyl group having 3 to 10 carbon atoms, and these may be, if desired, mono-, di- or tri-substituted by a substituent(s) selected from a halogen atom, an alkyl group, hydroxyl group, an alkyloxy group, amino group and an acylamino group.

Also, as the above-mentioned aryl group and the aryl portion, there may be mentioned phenyl group and a naphthyl group, and these may be, if desired, mono-, di- or tri-substituted by 1 to 3 substituents selected from an alkyl group, an alkyloxy group, an alkylenedioxy group, a dialkylaminoalkyloxy group, cyano group, a halogen atom, hydroxyl group, amino group, a mono-alkylamino group, a dialkylamino group, an acylamino group, trifluoromethyl group, an alkylthio group and carboxyl group.

The alkyl portion of the above-mentioned respective substituents may be either a straight or a branched, and if desired, these may be substituted by a substituent such as phenyl group, a phenylalkyl group, an aminoalkyl group, a cycloalkyl group and imidazolyl group.

Among the desired compounds (1) of the present invention, preferred compounds are compounds wherein $R^0$ is hydrogen atom, $R^1$ is an alkyl group, $R^2$ is an alkyl group, $OR^3$ is hydroxyl group, $R^4$ is hydrogen atom, W is oxygen atom, and the group represented by the formula (2):

is a mono- or di-substituted amino group, and particularly preferred are compounds wherein the group represented by the formula (2):

is a pyridyl-lower alkylamino group, an N,N-di(pyridyl-lower alkyl)amino group, an N-cycloalkyl-N-(phenyl-lower alkyl)amino group, an N-cycloalkyl-N-[(di-lower alkylamino)phenyl]amino group, an (aminophenyl)-piperadinyl group, an N-cycloalkylalkyl-N-(phenylalkyl) amino group, an N-cycloalkylalkyl-N-phenylamino group, an N-cycloalkylalkyl-N-[(di-lower alkylamino)phenyl] amino group, an N-[(aminocycloalkyl)alkyl]-N-phenylamino group or an N-pyridyl-N-(pyridyl-lower alkyl) amino group.

Among the desired compounds of the present invention, particularly preferred are 2-[3-(3-pyridylmethyl)ureido]-4-methoxy-6-tert-butylphenol, 2-(3-cyclohexyl-3-phenylmethylureido)-4-methoxy-6-tert-butylphenol, 2-[3-cycloheptyl-3-(4-dimethylaminophenyl)ureido]-4-methoxy-6-tert-butylphenol, 2-[3,3-di(pyridylmethyl)ureido]-4-methoxy-6-tert-butylphenol, 2-[4-(4-aminophenyl) piperazin-1-yl]amido-4-methoxy-6-tert-butylphenol, 2-[3-(2-cyclohexylethyl)-3-(4-dimethylaminophenyl)ureido]-4-methoxy-6-tert-butylphenol and 2-[3-(4-pyridylmethyl)-3-(3-pyridyl)ureido]-4-methoxy-6-tert-butylphenol.

In the phenol derivative (1) of the present invention, optical isomers based on an asymmetric carbon can be present, and the present invention includes both of the optical isomers and mixtures thereof.

The desired compound (1) of the present invention can be used for medical use in either a free form or in the form of a pharmaceutically acceptable salt. As such a pharmaceutically acceptable salt, there may be mentioned, for example, an inorganic salt such as a hydrochloride, sulfate, hydrobromide and phosphate, and an organic salt such as an acetate, fumarate, succinate, maleate, methanesulfonate and p-toluenesulfonate. Also, when the compound has a substituent such as a carboxyl group, it can be used in the form of a salt with a base (e.g., an alkali metal salt such as a sodium salt and a potassium salt, or an alkaline earth metal salt such as a calcium salt).

The desired compound (1) and the pharmaceutically acceptable salt thereof according to the present invention includes all of an intramolecular salt, adduct, complex, solvate and hydrate.

The desired compound (1) or a salt thereof of the present invention can be administered orally or parenterally, and according to the conventional manner, these can be used as a suitable pharmaceutical preparation such as a tablet, granule, capsule, powder, injection and inhalant.

An administration dose of the desired compound (1) or the pharmaceutically acceptable salt thereof according to the present invention may vary depending on the method of administration, age, body weight or conditions of a patient, but the administration dose per day is generally about 5 to 50 mg/kg in the case of an oral administration and about 0.1 to 10 mg/kg in the case of a parenteral administration.

The compound (1) or a pharmaceutically acceptable salt of the present invention can be prepared, for example, by the steps A) to E) as mentioned above.

In the above steps, as the salt of the amine compound (b) or the aniline compound (d), there may be used, for example, a salt with an inorganic acid such as hydrochloride and sulfate, and a salt with an inorganic base such as an alkali metal salt and an alkaline earth metal salt.

[Method A]

The condensation reaction of a compound (c) or a reactive derivative thereof and the amine compound (b) or a salt thereof can be carried out by a conventional method used for an amide-bond formation reaction in the presence or absence of a condensing agent such as 1,3-dicyclohexylcarbodiimide (DCC) and in the presence or absence of a base in a solvent or without a solvent.

As the base, there may be mentioned, for example, triethylamine, pyridine, dimethylaminopyridine, 1,8-diazabicyclo-[5.4.0]-7-undecene and diisopropylethylamine, and as the solvent, there may be mentioned, for example, dichloromethane, chloroform, 1,2-dichloroethane, diethyl ether, tetrahydrofuran, dioxane, ethylene glycol, dimethylformamide, dimethylsulfoxide, toluene and benzene.

Examples of the salt of the amine compound (b) include a salt with an inorganic acid such as hydrochloride and sulfate, and a salt with an inorganic base such as an alkali metal salt and an alkaline earth metal salt.

The above reaction can be carried out under cooling to under heating, and, for example, it can be suitably carried out at −30° to 100° C., particularly preferably at 0° to 50° C.

As the reactive derivative of the compound (c), there may be used a compound which is conventionally used in an amide-bond formation reaction such as a corresponding acid halide, mixed acid anhydride and active ester.

The above reaction can be carried out by using the amine compound (b) or a salt thereof in an amount of 0.2 to 3 mole, preferably 0.5 to 1.5 mole per mole of the compound (c) or a reactive derivative thereof.

When a phenyl carbamate (phenyl carbamic acid ester) derivative represented by the formula (c-1):

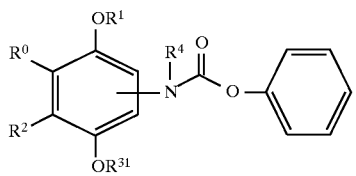

wherein the symbols have the same meanings as defined above,
is used as the reactive derivative of the compound (c), the reaction of the derivative (c-1) and the amine compound (b) or a salt thereof can be carried out in a suitable solvent. As the solvent, there may be suitably used, for example, benzene, toluene, xylene, dichloromethane, tetrahydrofuran and chloroform.

The above reaction suitably proceeds at 50° to 150° C., particularly at 50° to 100° C.

The reaction can be carried out by using the amine compound (b) or a salt thereof in an amount of 0.2 to 2.0 mole per mole of the phenyl carbamate derivative (c-1).
[Method B]

The reaction of the aniline compound (d) or a salt thereof and a reactive derivative of the carbamic acid compound (e) (e.g., an active ester such as phenyl ester) can be carried out in a suitable solvent such as benzene, cyclohexane, toluene, xylene, dichloromethane, chloroform, carbon tetrachloride, diethyl ether and tetrahydrofuran.

Examples of the salt of the aniline compound (d) include a salt with an inorganic acid such as hydrochloride and sulfate, and a salt with an organic acid such as methanesulfonate and p-toluenesulfonate.

The above reaction suitably proceeds at 50° to 150° C., particularly at 50° to 100° C.

The reaction can be carried out by using the reactive derivative of the carbamic acid compound (e) in an amount of 0.2 to 2.0 mole per mole of the aniline compound (d) or a salt thereof.
[Method C]

The reaction of the aniline compound (d) or a salt thereof and the isocyanate (or thioisocyanate) compound (f) can be carried out in a suitable solvent such as dichloromethane, chloroform, 1,2-dichloroethane, diethyl ether, tetrahydrofuran, dioxane, ethylene glycol, dimethylformamide, dimethylacetamide, dimethylsulfoxide, toluene, benzene, hexamethylphosphoramide, sulforan and 1,3-dimethyl-2-imidazolidinone or without a solvent.

As the aniline compound (d) or a salt thereof, there may be mentioned those as mentioned in the above Method B.

The above reaction suitably proceeds at −30° to 100° C., particularly at 0° to 50° C.

The reaction can be carried out by using the isocyanate (or thioisocyanate) compound (f) in an amount of 0.2 to 3.0 mole, preferably 0.5 to 1.5 mole per mole of the aniline compound (d) or a salt thereof.
[Method D]

The reaction of the compound (1-a) or (1-c) and the amine compound (g) can be carried out in the presence of a solvent (e.g., methanol, ethanol, dioxane, ethylene glycol, dimethylacetamide, benzene, toluene, chloroform, dichloromethane, dimethylsulfoxide and dimethylformamide) or in the absence of a solvent.

The above reaction can be suitably carried out at 0° to 200°° C., particularly at 25° to 100° C.

The reaction can be carried out by using the amine compound (g) in an amount of 0.2 to 10 mole, preferably 0.5 to 3 mole per mole of the compound (1-a) or (1-c).

In the above mentioned [Method A], [Method B], [method C] and [Method D], when $OR^{31}$ is a protected hydroxyl group, if desired, the protecting group for the said hydroxyl group may be removed according to the conventionally known method. Removal of the said protecting group can be carried out depending on the kind of the protecting group according to the conventionally known method such as hydrolysis, acid treatment or reduction.

When $OR^3$ of the desired compound (1) is hydroxyl group, if desired, the hydroxyl group can be protected by, for example, acylation according to the conventionally known method. The acylation reaction can be carried out according to the conventional manner by using, for example, a free acid of an amino acid, a cycloalkanoic acid or an alkanoic acid which may has a substituent, or a reactive derivative thereof.

As the reactive derivative thereof, there may be mentioned an acid halide, an acid anhydride, an activated amide or an activated ester.

The reaction can be carried out according to the conventional manner, and when, for example, an acid halide compound is used as an acylating agent, it can be suitably carried out in the presence of a base (e.g., triethylamine, pyridine, 4-N,N-dimethylaminopyridine, 1,8-diazabicyclo-[5.4.0]-7-undecene and sodium hydride) in a suitable solvent (e.g., dichloromethane, tetrahydrofuran and dimethylformamide) or without any solvent.

When a free acid is used as an acylating agent, the reaction is preferably carried out in the presence of a condensing agent which is conventionally used in an ester-bond formation reaction.

The protection of the hydroxyl group with a lower alkyloxycarbonyl group can be carried out in the same manner as in the above acylation reaction by using a halogenated-lower alkyl carbonate. Also, the conventionally used protecting group can be introduced into hydroxyl group according to the conventional manner.

The desired compound (1) of the present invention can be also prepared by mutually converting the obtained compound as mentioned above to another compound. Such a mutual conversion reaction of the desired compounds (1) can be optionally selected depending on the kind of a substituent in the compound (1), and, for example, the reaction can be carried out as mentioned in the following methods (a) to (c).
Method (a)

The compound (1) having a carboxyl group in the substituent $R^5$ or $R^6$ can be prepared by subjecting a corresponding derivative (1) having a protected carboxyl group (e.g., a carboxyl group protected by a protecting group such as an alkyl group and an arylalkyl group) to the conventional deprotection reaction of the protecting group such as a hydrolysis or hydrogenolysis.

The hydrolysis can be carried out, for example, in the presence of a base (e.g., an inorganic base such as sodium hydroxide). The hydrogenolysis can be carried out, for example in the presence of a catalyst such as palladium on an activated carbon under an atmosphere of hydrogen. The both deprotection reaction proceeds at 0° C. to 60° C.

Method (b)

The desired compound (1) having an amide group in the substituent $R^5$ or $R^6$ can be prepared by subjecting a corresponding compound (1) in which the substituent —$NR^5R^6$ of the compound (1) is a group containing a free carboxyl group and an amine compound represented by the formula (h):

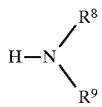
(h)

wherein —$NR^8R^9$ represents an amino group which may be mono- or di-substituted or a heterocyclic group containing nitrogen atom,
to condensation reaction.

The condensation reaction can be carried out in the presence of a dehydrating agent, and as the dehydrating agent, there may be used, for example, 1,3-dicyclohexylcarbodiimide (DCC). The reaction suitably proceeds at 0° to 50° C.

Method (c)

The desired compound (1) wherein the group —$NR^5R^6$ is a mono-alkyl substituted or di-alkyl substituted amino group can be prepared by allowing the compound (1) wherein the said group —$NR^5R^6$ is an unsubstituted or a mono-substituted amino group to react with an alkylating agent represented by the formula (i):

$$R^{10}\text{—}X \quad (i)$$

wherein $R^{10}$ represents an alkyl group which may be substituted and X represents a leaving group.

Alkylation can be carried out in the presence of an acid acceptor by reacting with an alkyl halide (e.g., alkyl chloride, and alkyl bromide and alkyl iodide), alkyl alkanesulfonate (e.g., alkyl methanesulfonate) or an alkyl arylsulfonate (e.g., alkyl toluenesulfonate).

As the acid acceptor, there may be suitably used an alkali metal hydroxide, alkali metal hydrogen carbonate, alkali metal carbonate and an organic base (e.g., triethylamine, diisopropylethylamine and pyridine). This reaction suitably proceeds at 0° to 50° C.

The solvent to be used in the reactions described in the above mentioned Methods (a) to (c) is not particularly limited so long as it is inert to the reaction, and may be suitably used, for example, dioxane, ethylene glycol, dimethylacetamide, dimethylformamide, hexamethylphosphoramide, benzene, tetrahydrofuran, toluene, ethyl acetate, a lower alcohol, dichloromethane, 1,2-dichloroethane, chloroform, carbon tetrachloride, 1,3-dimethyl-2-imidazolidinone, diethyl ether, dimethoxyethane, dimethylsulfoxide, carbon disulfide, acetone, water or a mixed solvent of the above.

The reactive derivative of the intermediate compound (c) according to the present invention such as a corresponding acid halide can be prepared by, for example, allowing an aniline compound represented by the formula (d):

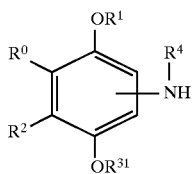
(d)

wherein the respective symbols have the same meanings as defined above,
or a salt thereof to react with phosgene, triphosgene or thiophosgene.

The reaction of the aniline compound (d) or a salt thereof and phosgene, triphosgene or thiophosgene can be suitably carried out in the presence of a base in a suitable solvent or without solvent.

As the base, there may be suitably used triethylamine, pyridine, 4-N,N-dimethylaminopyridine, 1,8-diazabicyclo-[5.4.0]-7-undecene and diisopropylethylamine, and as the solvent, there may be suitably used dichloromethane, chloroform, 1,2-dichloroethane, diethyl ether, tetrahydrofuran, dioxane, dimethylformamide, dimethylsulfoxide, toluene and benzene.

The reaction suitably proceeds at −30° to 100° C., particularly at 0° to 50° C.

The reaction can be carried out by using phosgene, triphosgene or thiophosgene in an amount of 0.2 mole to 5 mole, preferably 0.5 mole to 2 mole per mole of the aniline compound (d) or a salt thereof.

The starting compounds (b), (d) and (f) of the present invention can be prepared, for example, by the methods mentioned below.

Among these compounds, the aniline compound (d) wherein $R^4$ is hydrogen atom can be prepared by subjecting the compound represented by the formula (j):

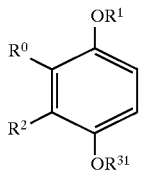
(j)

wherein the symbols have the same meanings as defined above,
to the introduction of an azo group or an azido group therein and then subjecting to reduction.

The aniline compound (d) wherein $R^4$ is an alkyl group or an acyl group can be prepared, if desired, by introducing one protecting group for the amino group of the aniline compound (d) wherein $R^4$ is hydrogen atom, allowing the resulting compound to react with a compound represented by the formula (n):

$$R^{41}\text{—}X \quad (n)$$

wherein X represents a halogen atom and $R^{41}$ represents an alkyl group or an acyl group,
and, if desired, removing the protecting group.

The amine compound (b) wherein the group represented by the formula (2):

(2)

is a mono- or di-substituted amino group can be prepared, for example, by allowing the compound represented by the formula (p):

$$R^{51}\text{—}NHZ^1 \quad (p)$$

wherein $Z^1$ represents a protecting group for amino group and other symbol has the same meaning as defined above,
to react with the compound represented by the formula (q):

$$R^{61}\text{—}Y \quad (q)$$

wherein $R^{61}$ represents a substituent (e.g., an alkyl group, an alkenyl group, an aryl group, an amino group or heterocyclic group) for amino group and Y represents a halogen atom,
and then removing the protecting group.

The compound (f) can be prepared, for example, by allowing the amine compound (b) wherein $R^6$ is hydrogen atom to react with phosgene, triphosgene or thiophosgene in the presence of a conventionally used base (e.g., triethylamine and pyridine).

The reactive derivative of the carbamic acid compound (e) or the phenyl carbamate derivative (c-1) can be prepared, for example, by allowing the amine compound (b) or the aniline compound (d) to react with phenyl chloroformate.

The compound (j) wherein $R^{31}$ is hydrogen atom can be prepared, for example, by treating the benzaldehyde derivative represented by the formula (k):

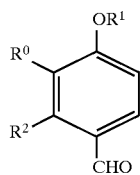

wherein the symbols have the same meanings as defined above,
with a peroxide such as hydrogen peroxide (Baeyer-Villiger Reaction), and then subjecting the resulting compound to hydrolysis.

Further, the compound (k) can be prepared by a conventional manner, for example, by halogenating the compound represented by the formula (m):

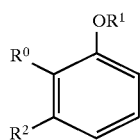

wherein the symbols have the same meanings as defined above,
with bromine, etc., followed by lithionating the halogenated product andated product and then subjecting the resulting compound to formylation with N,N-dimethylformamide and the like.

When the compound represented by the formula (d), (c-1) or (j) has hydroxyl group, the hydroxyl group can be protected by a protecting group such as methoxymethyl group, if desired, in each of the steps for preparing the compound (1). Also, the said protecting group can be easily removed by the conventional manner such as a treatment with an acid (e.g., hydrochloric acid).

As the protecting group for the amino group, there may be mentioned a conventionally used protecting group which is available for protection of the amino group such as benzyloxycarbonyl group and tert-butoxycarbonyl group.

The desired compound (1) of the present invention can be converted into a pharmaceutically acceptable salt by the conventional manner, if desired.

In the present specification, as the alkyl group and alkyl portion, there may be mentioned an alkyl group and an alkyl portion having 1 to 20 carbon atoms, preferably 1 to 10 carbon atoms, particularly 1 to 6 carbon atoms. As the lower alkyl group and lower alkyl portion, there may be mentioned those having 1 to 6 carbon atoms, particularly 1 to 4 carbon atoms. As the alkenyl group, there may be mentioned that having 2 to 20 carbon atoms, particularly 2 to 7 carbon atoms. As the lower alkenyl group and lower alkenyl portion, there may be mentioned those having 2 to 8 carbon atoms, particularly 2 to 5 carbon atoms. As the cycloalkyl group, there may be mentioned that having 3 to 10 carbon atoms, particularly 5 to 8 carbon atoms. As the halogen atom, there may be mentioned chlorine atom, bromine atom, fluorine atom or iodine atom. As the aryl group, there may be mentioned, for example, a phenyl group and a naphthyl group. As the alkylenedioxy group, there may be mentioned an alkylenedioxy group having 1 to 6 carbon atoms.

EXAMPLES

In the following, specific synthetic methods of the compounds according to the present invention are described as examples.

Example 1

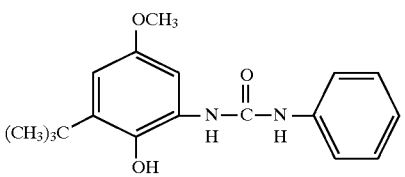

(1) A tetrahydrofuran (THF) (20 ml) containing 2.4 g of (2-amino-4-methoxy-6-tert-butylphenoxy)methoxymethane and 1.09 ml of phenyl isocyanate was stirred at room temperature for 3 hours, and then the solvent was removed under reduced pressure. The obtained residue was crystallized from hexane, and recrystallized from an ethyl acetate-hexane mixed solution to give 2.3 g of [2-(3-phenylureido)-4-methoxy-6-tert-butylphenoxy]methoxymethane (yield: 64%, melting point: 121°–123° C., IR: 3300, 1650 $cm^{-1}$).

NMR (δ ppm, $CDCl_3$): 1.34 (9H, s), 3.55 (3H, s), 3.78 (3H, s), 4.95 (2H, s), 6.60 (1H, d, J=3 Hz), 6.81 (1H, s), 7.03–7.41 (5H, m), 7.63 (1H, d, J=3 Hz), 8.05 (1H, s)

(2) Conc. hydrochloric acid (1.5 ml) was added to 30 ml of a methanol solution containing 2.2 g of [2-(3-phenylureido)-4-methoxy-6-tert-butylphenoxy]methoxymethane and the mixture was stirred at room temperature for 1.5 hours. The solvent was removed under reduced pressure and the residue was extracted with ethyl acetate. The extract was washed and dried, and the solvent was removed under reduced pressure. Hexane was added to the residue and the resulting crystals were collected by filtration and recrystallized from a mixed solution of ethyl acetate and hexane to give 1.6 g of 2-(3-phenylureido)-4-methoxy-6-tert-butylphenol (yield: 83%, melting point: 147°–149° C., IR: 3400, 3350, 1670 $cm^{-1}$).

NMR (δ ppm, $CDCl_3$): 1.4 (9H, s), 3.67 (3H, s), 6.38 (1H, d, J=3 Hz), 6.77 (1H, d, J=3 Hz), 6.84 (1H, s), 7.05–7.33 (6H, m), 7.65 (1H, s)

Examples 2 to 13

The corresponding starting materials and phenyl isocyanate or phenyl isothiocyanate were treated in the same manner as described in Example 1 to give the compounds as shown in Tables 1 and 2.

TABLE 1

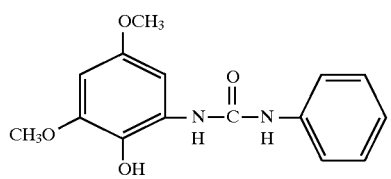

| Example | R²— | W | Melting point (°C.) |
|---|---|---|---|
| 2 | CH₃— | O | 173–176 |
| 3 | CH₃(CH₂)₇— | O | 100–101 |
| 4 | CH₃O— | O | 172–174 |
| 5 | CH₃(CH₂)₇O— | O | 66–68 |
| 6 | CH₃(CH₂)₇O— | S | 114–116 |
| 7 | CH₃(CH₂)₁₃O— | O | 64–67 |
| 8 | CH₃(CH₂)₁₃— | O | 111–113 |
| 9 | CH₃O— | S | 131–134 |
| 10 | CH₃CH₂— | O | 150–152 |
| 11 | (CH₃)₃C— | S | 134–136 |

(Note) each symbol represents the following:
Me: methyl group
Et: ethyl group
Pr: propyl group
Bu: butyl group
Ph: phenyl group
Boc: tert-butyloxycarbonyl group hereinafter the symbols represent the same.

TABLE 2

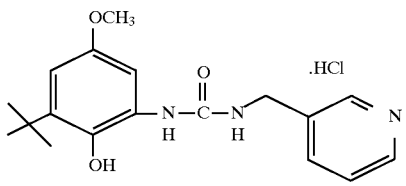

| Example | R¹— | W | Melting point (°C.) |
|---|---|---|---|
| 12 | CH₃(CH₂)₇— | O | 115–117 |
| 13 | CH₃(CH₂)₁₅— | O | 157–159 |

Example 14

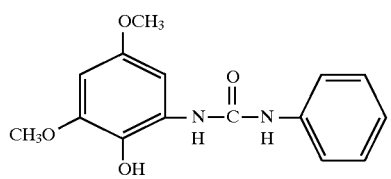

(3-Amino-4,6-dimethoxyphenoxy)methoxymethane and phenyl isocyanate were treated in the same manner as described in Example 1 to give 3-(3-phenylureido)-4,6-dimethoxyphenol (melting point: 162°–164° C.).

Example 15

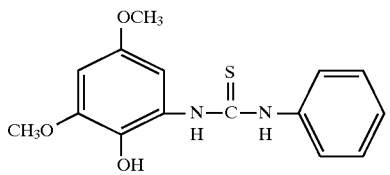

(3-Amino-4,6-dimethoxyphenoxy)methoxymethane and phenyl isothiocyanate were treated in the same manner as described in Example 1 to give 3-(3-phenylthioureido)-4,6-dimethoxyphenol (melting point: 152°–154° C.).

Example 16

(1) A dichloromethane (450 ml) solution containing 5.58 g of triphosgene was cooled to −78° C., and after dropping 150 ml of a dichloromethane solution containing 11.25 g of (2-amino-4-methoxy-6-tert-butylphenoxy)methoxymethane and 20 ml of triethylamine. The temperature of the mixture was raised to 0° C. and the solvent was removed under reduced pressure. To the residue was added 200 ml of dichloromethane, and then 100 ml of a dichloromethane solution containing 5.08 g of 3-aminomethylpyridine and 10 ml of triethylamine was added dropwise to the mixture. The resulting mixture was further stirred for one hour. The reaction mixture was washed and dried, and the solvent was removed under reduced pressure. The residue was purified by silica gel column chromatography (solvent; chloroform:methanol=15:1), and crystallized from isopropyl ether and further recrystallized from a mixed solution of isopropyl ether and ethyl acetate to give 13.97 g of {2-[3-(3-pyridylmethyl)ureido]-4-methoxy-6-tert-butylphenoxy}methoxymethane (yield: 80%, melting point: 108°–109° C.).

(2) To 150 ml of a methanol solution containing 13.97 g of the above product was added 6.8 ml of conc. hydrochloric acid, and the mixture was stirred at room temperature for one hour. The reaction mixture was evaporated to dryness under reduced pressure and the crystalline residue was recrystallized from an ethanol solution to give 11.20 g of 2-[3-(3-pyridylmethyl)ureido]-4-methoxy-6-tert-butylphenol hydrochloride (yield: 82%, melting point: 165°–167° C.).

Examples 17 to 50

The corresponding starting materials were treated in the same manner as described in Example 16 to give the compounds as shown in Tables 3 to 8.

TABLE 3

[Structure: 3-methoxy-5-t-butyl-6-hydroxyphenyl-NH-C(=W)-NH-R⁶]

| Example | —R⁶ | W | Melting point (°C.) |
|---------|-----|---|---------------------|
| 17 | —(CH₂)₃—N(piperazine)N—CH(Ph)₂ | O | 173–175 |
| 18 | —(CH₂)₂CH(OH)CH₂OH | O | 118–123 |
| 19 | —(CH₂)₂—N(piperazine)N—Ph | O | 134–135 |
| 20 | 4-OMe-2-t-Bu-6-hydroxyphenyl | O | 153–154 |
| 21 | 3-methyl-1-(3-trifluoromethylphenyl)-4,5-dihydro-1H-pyrazol-5-yl | O | 178–188 |
| 22 | —(CH₂)₂—C₆H₄—O—(CH₂)₃—N(n-Bu)₂ | O | 134–136 |
| 23 | —CH₂CH₂Cl | O | 126–128 |
| 24 | 4-(n-C₈H₁₇)phenyl | O | 86–87 |
| 25 | 2,4-difluorophenyl | O | 153–154 (decomposed) |
| 26 | 2,6-di-i-Pr-phenyl | O | 193–195 (decomposed) |
| 27 | —C(CH₂OH)₃ | O | 169–170 |
| 28 | —C(CH₃)(CH₂OH)₂ | O | 137–139 |

TABLE 3-continued

Structure: 3-t-Bu, 5-OMe, 2-OH phenyl-NH-C(=W)-NH-R⁶

| Example | –R⁶ | W | Melting point (°C.) |
|---|---|---|---|
| 29 | cyclohexyl | O | 147–148 (decomposed) |
| 30 | –CH₂–(4-piperidinyl, N-C(=O)-NH-[3-t-Bu,5-OMe,2-OH-phenyl]) | O | 150–152 |
| 31 | –CH(CH₂)₅COOEt, phenyl | O | 93–95 |
| 32 | –CHCOOMe (S), benzyl | O | Powder IR: 3374, 1742, 1650, 1560 (cm⁻¹) |
| 33 | (CH₂)₄NH–CO–OCH₂Ph / –CHCOOMe (S) | O | Oily product IR: 3300, 1690, 1645, 1557 (cm⁻¹) |

TABLE 4

Structure: 3-t-Bu, 5-OMe, 2-OH phenyl-NH-C(=S)-NH-R⁶

| Example | –R⁶ | Melting point (°C.) |
|---|---|---|
| 34 | 3-t-Bu, 5-OMe, 2-OH phenyl | 135–137 |

TABLE 5

[Structure: 3-tert-butyl-5-methoxy-2-hydroxyphenyl group attached to NH-C(=W)-NH-R⁶·HCl]

| Example | −R⁶ | W | Melting point (°C.) |
|---|---|---|---|
| 35 | 3-pyridyl | O | 200–202 (decomposed) |
| 36 | 4-(NMe₂)phenyl | O | 196–199 |
| 37 | 4-pyridyl | O | 193–195 |
| 38 | −CH₂-(4-pyridyl) | O | 118–120 |
| 39 | 2-pyridyl | O | 185–187 |
| 40 | −(CH₂)₂-(2-pyridyl) | O | 152–154 |
| 41 | −CH₂-(2-pyridyl) | O | 175–176 |
| 42 | −(CH₂)₂-(3-pyridyl) | O | 172–175 |
| 43 | −(CH₂)₂−C₆H₄−O−(CH₂)₃−N(n-Bu)₂ | O | 150–153 |

TABLE 6

[Structure: 2-OH, 3-t-Bu, 5-OMe phenyl with NH-C(=W)-NH-R⁶·2HCl]

| Example | −R⁶ | W | Melting point (°C.) |
|---|---|---|---|
| 44 | −(CH₂)₂−N(piperazinyl)N−CHPh₂ | O | 169–175 (decomposed) |
| 45 | −(CH₂)₃−N(piperazinyl)N−(CH₂)₃−NH−C(=O)−NH−(5-OMe, 3-t-Bu, 2-OH phenyl) | O | 191–193 |

TABLE 7

[Structure: 2-OH, 3-OMe, 5-OMe phenyl with NH-C(=W)-NH-R⁶·HCl]

| Example | −R⁶ | W | Melting point (°C.) |
|---|---|---|---|
| 46 | −(CH₂)₂−NH−CHPh₂ | O | 183–185 |

TABLE 8

[Structure: 2-OH, 3-t-Bu, 5-OMe phenyl with NH-C(=O)-NH-R⁶]

| Example | −R⁶ | Melting point (°C.), etc. |
|---|---|---|
| 47 | −NH−Ph | 160–162 |
| 48 | −NHSO₂−Ph | 198–199 (decomposed) |

TABLE 8-continued

[Structure: 2-OH, 3-t-Bu, 5-OMe phenyl with NH-C(=O)-NH-R⁶]

| Example | −R⁶ | Melting point (°C.), etc. |
|---|---|---|
| 49 | −N(CH₃)₂ | 150–153 monohydrochloride |
| 50 | −NH−C(=O)−NH−(5-OMe, 3-t-Bu, 2-OH phenyl) | 175–176 |

Example 51

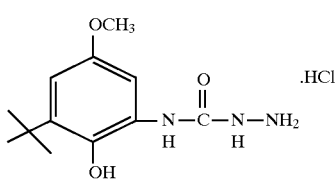

(1) A mixed solution comprising 25 ml of 1.847M phosgenedichloromethane and 130 ml of dichloromethane was cooled to −78° C., and to the solution was added dropwise a mixture comprising 5.5 g of (2-amino-4-methoxy-6-tert-butylphenoxy)methoxymethane, 9.6 ml of triethylamine and 50 ml of dichloromethane. After the reaction, the temperature of the mixture was raised to 0° C. and the solvent was removed under reduced pressure. The residue was dissolved in 70 ml of dimethylformamide (DMF) and the solution was added dropwise to a mixture of 3.45 g of hydrazine monohydrate, 4.8 ml of triethylamine and 70 ml of DMF, and the mixture was stirred at room temperature for 2 hours. Water was added to the reaction mixture and the reaction mixture was extracted with ethyl acetate. The extract was washed and dried, and the solvent was removed under reduced pressure. The residue was purified by silica gel column chromatography (solvent; ethyl acetate) and recrystallized from a mixed solution of isopropyl ether and ethyl acetate to give 3.5 g of [2-(3-aminoureido)-4-methoxy-6-tert-butylphenoxy]methoxymethane (yield: 51%, melting point: 132°–134° C.).

(2) Conc. hydrochloric acid (3 ml) was added to 50 ml of a methanol solution containing 3.40 g of the above product, and the mixture was stirred at room temperature for 5 hours. The reaction mixture was evaporated to dryness under reduced pressure, an aqueous saturated sodium hydrogen carbonate solution was added to the residue to neutralize the mixture and the mixture was extracted with ethyl acetate. The extract was washed and dried, and the solvent was removed under reduced pressure. The crystalline residue was recrystallized from a mixed solution of isopropyl ether and ethyl acetate. The resulting crystals were dissolved in 20 ml of dichloromethane, and after adding 3.8 ml of 4N-hydrogen chloride-dioxane solution, and the mixture was evaporated to dryness under reduced pressure. Hexane was added to the residue to give 2.18 g of 2-(3-aminoureido)-4-methoxy-6-tert-butylphenol hydrochloride as colorless powder (yield: 66%).

Example 52

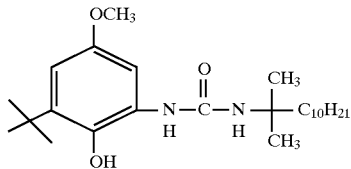

(1) Isobutyric acid (13.9 ml) was added dropwise to a mixture of 21.1 ml of 62.5% sodium hydride, 93.8 ml of diisopropylamine and 150 ml of tetrahydrofuran (THF) at 30° C. or lower. After refluxing the mixture for 30 minutes, to the mixture was added 31.0 ml of a 1.6M n-butyl lithium-hexane solution at 10° C. or lower and the mixture was stirred for 15 minutes at the same temperature and for 2 hours at room temperature. At 10° C. or lower, 5.76 g of 1-bromodecane was added dropwise to the mixture. The mixture was stirred at the same temperature for one hour and then at room temperature overnight. After adding 300 ml of ice water, the reaction mixture was washed with diethyl ether, and the aqueous layer was adjusted to pH=1 with conc. hydrochloric acid and extracted with isopropyl ether. After the extract was washed and dried, the solvent was removed under reduced pressure to give 2.36 g of 2,2-dimethyllauric acid (state: pale yellow oily product).

NMR (δ ppm, CDCl$_3$): 0.88 (3H, t, J=3 Hz), 1.49 (6H, s) 1.10–1.65 (18H, m)

(2) A mixture of 5 g of 2,2-dimethyllauric acid, 4.72 ml of diphenylphosphorylazide (DPPA), 3.36 ml of triethylamine and 80 ml of benzene was refluxed for one hour. After cooling, a mixed solution of 5.763 g of (2-amino-4-methoxy-6-tert-butylphenoxy)methoxymethane and 20 ml of benzene was added dropwise to the above mixture. The resulting mixture was stirred at room temperature for one hour and then under reflux for 10 hours. Water was added to the reaction mixture, and the reaction mixture was extracted with ethyl acetate. The extract was washed and dried, and the solvent was removed under reduced pressure. The residue was purified by silica gel column chromatography (solvent; hexane:ethyl acetate=4:1) and the product was recrystallized from hexane to give 2.89 g of {2-[3-(1,1-dimethylundecyl)ureido]-4-methoxy-6-tert-butylphenoxy}methoxymethane (melting point: 83°–85° C.).

(3) The product (2.75 g) thus obtained was dissolved in 50 ml of methanol, and after adding 1 ml of conc. hydrochloric acid, the mixture was stirred at room temperature for one hour. The solvent was removed under reduced pressure, water was added to the residue and the mixture was extracted with ethyl acetate. The extract was washed and dried, and the solvent was removed under reduced pressure. Hexane was added to the crystalline residue and the crystals were collected by filtration to give 0.778 g of 2-[3-(1,1-dimethylundecyl)ureido]-4-methoxy-6-tert-butylphenol (melting point: 99°–102° C.).

Example 53

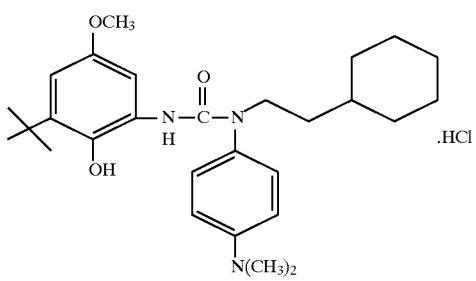

(1) A dichloromethane (100 ml) solution of 1.494 g of triphosgene was cooled to −78° C., and to the solution was added dropwise a mixture of 3.012 g of (2-amino-4-methoxy-6-tert-butylphenoxy)methoxymethane, 5.3 ml of triethylamine and 60 ml of dichloromethane. The temperature of the mixture was raised to 0° C., and the solvent was removed under reduced pressure. At room temperature, 100 ml of dichloromethane was added to the residue, and a mixture of 3.101 g of (2-cyclohexylethyl)-(4-dimethylaminophenyl)-amine, 2.6 ml of triethylamine and 50 ml of dichloromethane was added dropwise. The mixture was further stirred at room temperature overnight. The reaction mixture was washed and dried, the solvent was removed under reduced pressure. The residue was purified by silica gel column chromatography (solvent; chloroform::ethyl acetate=15:1) and recrystallized from an isopropyl ether solution to give 3.3 g of {2-[3-(2-cyclohexylethyl)-3-(4-dimethyl-aminophenyl)ureido]-4-methoxy-6-tert-butylphenoxy}methoxymethane (yield: 51%, melting point: 108°–110° C.).

(2) Conc. hydrochloric acid (3 ml) was added to a mixed solution of 3.183 g of the product thus obtained, 50 ml of methanol and 10 ml of dichloromethane, and the mixture was stirred at room temperature for 3 hours. The reaction mixture was evaporated to dryness under reduced pressure. An aqueous saturated sodium hydrogen carbonate solution was added to the residue and the mixture was extracted with ethyl acetate. The extract was washed with water and dried, and the solvent was removed under reduced pressure. The residue was dissolved in 20 ml of dichloromethane, and after adding 5 ml of 4N-hydrogen chloride-dioxane solution, the mixture was evaporated to dryness under reduced pressure. The residue was recrystallized from an ethyl acetate solution to give 1.63 g of 2-[3-(2-cyclohexylethyl)-3-(4-dimethylaminophenyl)ureido]-4-methoxy-6-tert-butylphenol hydrochloride (yield: 52%, melting point: 112°–116° C.).

Examples 54 to 132

The corresponding starting materials were treated in the same manner as described in Example 53 to give the compounds as shown in Tables 9 to 18.

TABLE 9

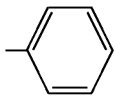

| Example | —R⁵ | —R⁶ | Melting point (°C.), etc. |
|---|---|---|---|
| 54 | 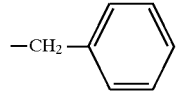 | —CH₂CH=C(CH₂)₂CH=C(CH₃)₂<br>(Z) \|<br>CH₃ | 130–132 |
| 55 | —CH₂—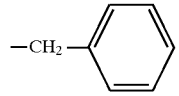 | —(CH₂)₆CH₃ | 75–77 |
| 56 | —CH₂— | 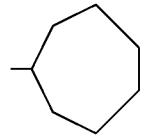 | 140–141 |
| 57 | 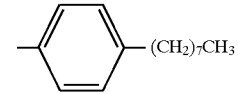 | 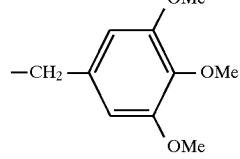—(CH₂)₇CH₃ | 68–70 |
| 58 | 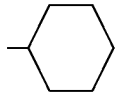 | 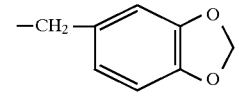 | Powder<br>IR: 3370,<br>1620, 1594<br>(cm⁻¹) |
| 59 | —CH₂—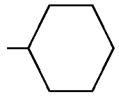 | 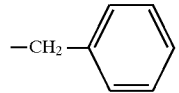 | 153–154 |
| 60 | —CH₂—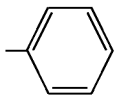 | 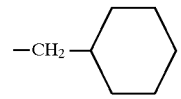 | 142–144 |
| 61 | 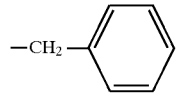 | —CH₂—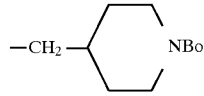 | 124–126 |
| 62 | —CH₂— | —CH₂—NBoc | 158–160 |

TABLE 9-continued
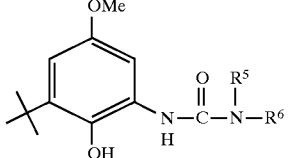
| Example | −R⁵ | −R⁶ | Melting point (°C.), etc. |
|---|---|---|---|
| 63 | −CH₂−Ph | −CH₂−cyclohexyl | 122–125 |
| 64 | −Ph | −(CH₂)₂−cyclohexyl | 116–118 |
| 65 | −CH₂−Ph | cycloheptyl | 141–142 |
| 66 | −CH₂−Ph | cyclopentyl | 129–130 |
| 67 | −CH₂−Ph | cyclohexyl-NHBoc | 144–148 |
| 68 | cycloheptyl | 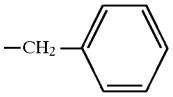 | 121–123 |
| 69 | −C₆H₄−NHBoc | cycloheptyl | Powder IR: 3336, 1730, 1629, 1518 (cm⁻¹) |
| 70 | 3,4,5-tri-OMe-C₆H₂− | −(CH₂)₂−cyclohexyl | 148–150 |
| 71 | −CH₂−(3,4-di-OMe-C₆H₃) | cyclohexyl | 136–138 |

TABLE 9-continued
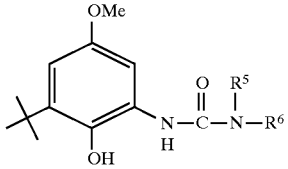
| Example | —R⁵ | —R⁶ | Melting point (°C.), etc. |
|---|---|---|---|
| 72 | 3,4,5-tri-OMe-phenyl | cycloheptyl | 164–166 |
| 73 | 3-CF₃-phenyl | cycloheptyl | 144–147 |
| 74 | —CH₂Ph | —CH₂-(4-piperidyl)-N-C(=O)—O—CH₂Ph | 120–121 |
| 75 | 4-SMe-phenyl | cycloheptyl | 118–119 |
| 76 | 4-F-phenyl | cycloheptyl | 140–142 |
| 77 | 4-OMe-phenyl | cycloheptyl | 137–139 |
| 78 | —(CH₂)₃NMe₂ | cycloheptyl | 91–93 |
| 79 | 4-NMe₂-phenyl | —CH(Ph)₂ | 165–167 |
| 80 | 3-pyridyl | —(CH₂)₅COOEt | 132–134 |
| 81 | phenyl | —(CH₂)₃COOEt | Oily product IR: 3340, 2955, 1732, 1639 (cm⁻¹) |

TABLE 9-continued
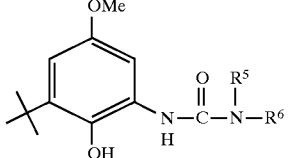
| Example | —R⁵ | —R⁶ | Melting point (°C.), etc. |
|---|---|---|---|
| 82 | 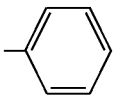 | —(CH₂)₂COOEt | 63–70 |
| 83 | —(CH₂)₃COOEt | 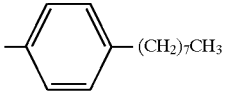 (CH₂)₇CH₃ | Powder IR: 1730, 1638 (cm⁻¹) |
| 84 | —(CH₂)₃COOEt | 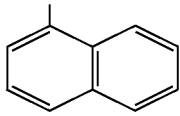 | 104–105 |
| 85 | —(CH₂)₃COOEt | 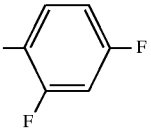 | 115–116 |
| 86 | —(CH₂)₃COOEt | 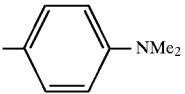 NMe₂ | 77–79 |
| 87 | —(CH₂)₃COOEt | 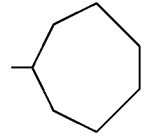 | 99–101 |
| 88 | —(CH₂)₃COOEt | 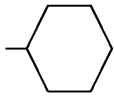 | 113–115 |
| 89 | —(CH₂)₃COOEt |  | 119–120 |
| 90 | —H | —(CH₂)₃COOEt | 69–71 |
| 91 | 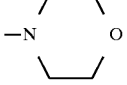 | 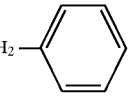 | 169–171 |
| 92 | 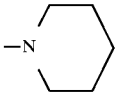 | 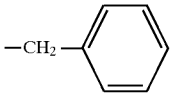 | 124–127 |
| 93 | 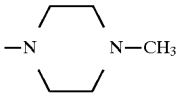 | 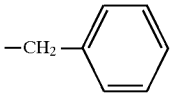 | Monohydrochloride 184–186 |

TABLE 10
| Example | —R⁵ | —R⁶ | Melting point (°C.) |
|---|---|---|---|
| 94 | 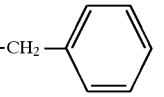 | 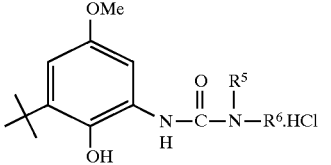 | 130–132 |
TABLE 11
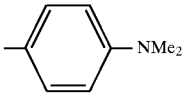
| Example | —R⁵ | —R⁶ | Melting point (°C.), etc. |
|---|---|---|---|
| 95 | 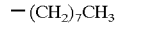 | —(CH₂)₇CH₃ | 156–159 |
| 96 | 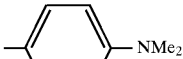 | 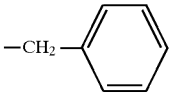 | 183–185 |
| 97 | 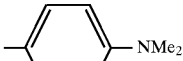 | 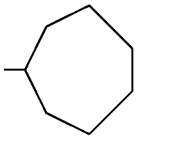 | 140–142 |
| 98 | 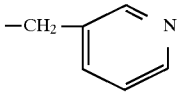 | 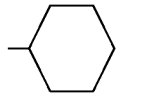 | Powder IR: 3240, 1610 (cm⁻¹) |
| 99 | 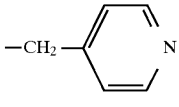 | 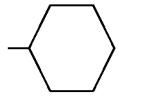 | Powder IR: 3370, 1639 (cm⁻¹) |
| 100 | 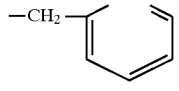 | 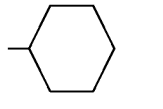 | Powder IR: 3240, 1616 (cm⁻¹) |
| 101 | 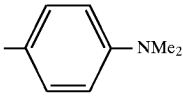 | 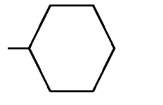 | 173–175 (decomposed) |

TABLE 11-continued
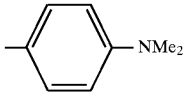
| Example | —R⁵ | —R⁶ | Melting point (°C.), etc. |
|---|---|---|---|
| 102 | 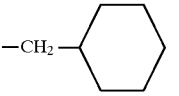 | —CH₂—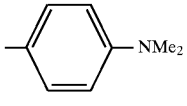 | 186–188 |
| 103 |  | 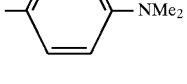 | 166–167 |
| 104 | 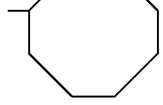 | 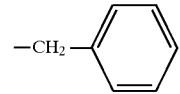 | 143–145 |
| 105 | —CH₂—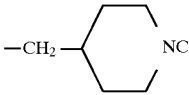 | —CH₂—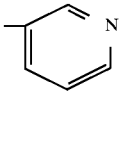NCH₂Ph | Powder IR: 3400, 1625 (cm⁻¹) |
| 106 | 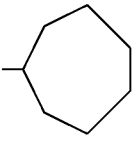 | 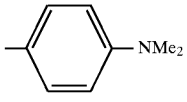 | 146–148 |
| 107 | 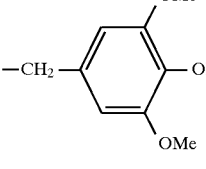 | —CH₂—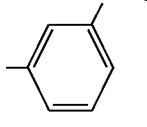 | Powder IR: 3380, 1630, 1594, 1510 (cm⁻¹) |
| 108 | 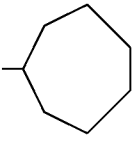 | 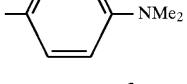 | 135–138 |
| 109 |  | —(CH₂)₆CH₃ | 144–147 |
| 110 | —CH₂—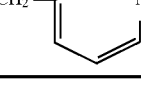 | —CH₂—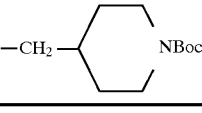NBoc | Powder IR: 3450, 1668, 1535, 1471 (cm⁻¹) |

TABLE 12
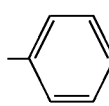
| Example | —R⁵ | —R⁶ | Melting point (°C.) |
|---|---|---|---|
| 111 |  | 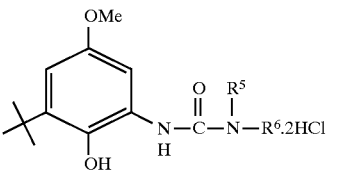 | 153–154 |
TABLE 13
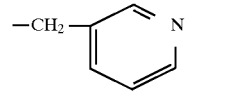
| Example | —R⁵ | —R⁶ | Melting point (°C.), etc. |
|---|---|---|---|
| 112 | 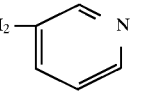 |  | 113–120 |
| 113 | 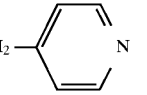 | 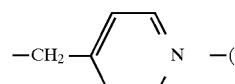 | 148–155 |
| 114 | 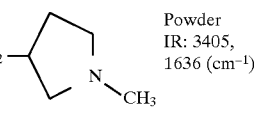 | 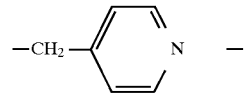 | Powder IR: 3405, 1636 (cm⁻¹) |
| 115 | 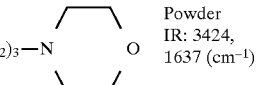 | 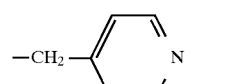 | Powder IR: 3424, 1637 (cm⁻¹) |
| 116 | 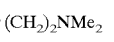 | —(CH₂)₂NMe₂ | 150–152 |
| 117 | 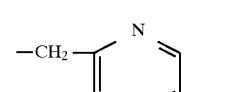 | 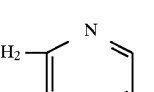 | Powder IR: 3428, 1618 (cm⁻¹) |
| 118 | 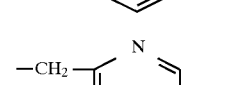 | 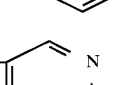 | 167 |

TABLE 13-continued

[Structure: 3-tert-butyl-5-methoxy-2-hydroxyphenyl urea derivative with -N(R⁵)-R⁶·2HCl]

| Example | —R⁵ | —R⁶ | Melting point (°C.), etc. |
|---|---|---|---|
| 119 | —CH₂-(4-pyridyl) | -(3-pyridyl) | Powder IR: 3417, 1641, 1620 (cm⁻¹) |
| 120 | —CH₂-(3-pyridyl) | -(3-pyridyl) | Powder IR: 3424, 1656, 1611, 1557 (cm⁻¹) |
| 121 | —CH₂-(4-pyridyl) | —CH₂-(2-pyridyl) | Powder IR: 3406, 1638, 1530, 1469 (cm⁻¹) |
| 122 | —CH₂-(3-pyridyl) | —CH₂-(4-pyridyl) | Powder IR: 3430, 1638, 1472 (cm⁻¹) |
| 123 | —CH₂-(2-pyridyl) | —CH₂-(3-pyridyl) | Powder IR: 3416, 1630, 1540, 1469 (cm⁻¹) |

TABLE 14

[Structure: 3-tert-butyl-5-methoxy-2-hydroxyphenyl urea derivative with -N(R⁵)-R⁶]

| Example | —N(R⁵)—R⁶ | Melting point (°C.), etc. |
|---|---|---|
| 124 | 1,2,3,4-tetrahydroisoquinolin-2-yl | Powder IR: 3300, 1625, 1520 (cm⁻¹) |
| 125 | 4-(4-nitrophenyl)piperazin-1-yl | Monohydrochloride 159–160 |

TABLE 15

[Structure: 3-tert-butyl-5-methoxy-2-hydroxyphenyl urea derivative with -N(R⁵)-R⁶·HCl]

| Example | —N(R⁵)—R⁶ | Melting point (°C.) |
|---|---|---|
| 126 | 4-(benzylaminomethyl)piperidin-1-yl | 148–150 |

TABLE 16

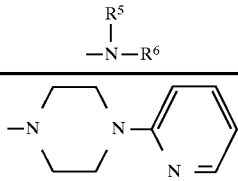

| Example | —N(R⁵)—R⁶ | Melting point (°C.) |
|---|---|---|
| 127 | —N(piperazinyl)-2-pyridyl | 164–165 |

TABLE 17

[Structure: 2-OR¹, 4-R² phenol with —N(H)—C(=O)—N(cyclohexyl)—CH₂—phenyl]

| Example | —R¹ | —R² | Melting point (°C.), etc. |
|---|---|---|---|
| 128 | —CH₃ | —OCH₃ | Powder IR: 3370, 1625 (cm⁻¹) |
| 129 | —(CH₂)₅CH₃ | —C(CH₃)₃ | 118–120 |
| 130 | —CH(CH₃)₂ | —C(CH₃)₃ | 142–143 |
| 131 | —CH₂CH₃ | —C(CH₃)₃ | 148–149 |

TABLE 18

[Structure: 2-OR¹, 4-R² phenol with —N(H)—C(=O)—N(cycloheptyl)—(4-N(CH₃)₂-phenyl)·HCl]

| Example | —R¹ | —R² | Melting point (°C.), etc. |
|---|---|---|---|
| 132 | —CH₂CH₃ | —C(CH₃)₃ | 137–141 (decomposed) |

Example 133

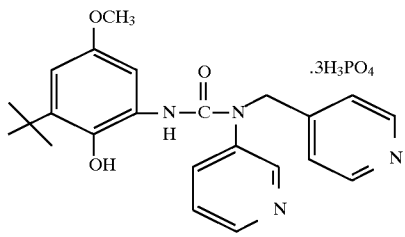

Ethanol (1000 ml) was added to 97.8 g of 2-[3-(4-pyridylmethyl)-3-(3-pyridyl)ureido]-4-methoxy-6-tert-butylphenol, and after dissolving the mixture under heating. An ethanol solution (450 ml) of 71.92 g of phosphoric acid was added dropwise to the above solution. After cooling the said solution, precipitated crystals were collected by filtration, washed with ethanol and dried to give 143.1 g of colorless crude crystals. After 950 ml of acetone was added to the said crystals, and the mixture was dissolved by adding 500 ml of water while heating. After cooling the said solution, precipitated crystals were collected by filtration and dried to give 101.9 g of 2-[3-(4-pyridylmethyl)-3-(3-pyridyl)ureido]-4-methoxy-6-tert-butylphenol triphosphate (yield: 60%, melting point: 196°–198° C.).

Example 134

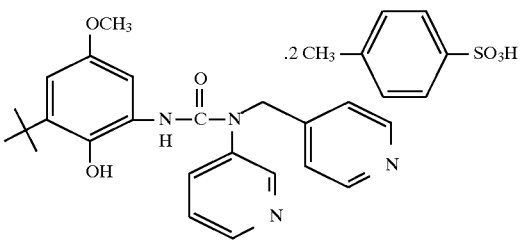

Ethyl acetate (4 ml) was added to 100 mg of 2-[3-(4-pyridylmethyl)-3-(3-pyridyl)ureido]-4-methoxy-6-tert-butylphenol and the mixture was heated. 94 mg of p-toluenesulfonic acid was added to the above solution. After cooling the solution, the solvent was removed under reduced pressure and the residue was crystallized from an ethanol solution to give 129 mg of 2-[3-(4-pyridylmethyl)-3-(3-pyridyl)ureido]-4-methoxy-6-tert-butylphenol di-p-toluenesulfonate (yield: 70%, melting point: 124°–128 C.).

Example 135

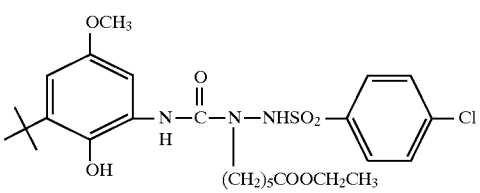

(1) A mixture of 25 g of tert-butoxycarbonyl hydrazine, 37 g of ethyl 6-bromohexanoate, 26 g of potassium carbonate and 40 ml of hexamethylphosphoramide (HMPA) was stirred at room temperature for 3.5 hours. Water was added to the mixture, and the resulting mixture was extracted with ethyl acetate. The organic layer was washed and dried, and the solvent was removed under reduced pressure. The residue was purified by silica gel column chromatography (solvent; chloroform:ethyl acetate=3:1) to give 16 g of ethyl 6-(N'-tert-butoxycarbonylhydrazino)hexanoate (state: oily product, IR: 3350, 1740, 1720 cm⁻¹).

(2) To 12 g of ethyl 6-(N'-tert-butoxycarbonylhydrazino)hexanoate was added 20 ml of a 15% hydrogen chloridedioxane solution, and the mixture was stirred at room temperature for 3 hours. Ether (diethyl ether) was added to the mixture, and precipitated crystals were collected by filtration and washed with ether to give 6.3 g of ethyl 6-hydrazinohexanoate hydrochloride (yield: 68%, IR (KBr): 1740 cm⁻¹).

(3) A mixture of 19.1 ml of 2.464M phosgene-dichloromethane solution and 200 ml of dichloromethane was cooled to −78° C., and to the mixture was added dropwise a mixture of 7.04 g of (2-amino-4-methoxy-6-tert-butylphenoxy)methoxymethane, 8.9 g of triethylamine and 70 ml of dichloromethane to the above solution. The temperature of the resulting mixture was raised to 0° C. and the solvent was removed under reduced pressure. To the residue was added 100 ml of dimethylformamide (DMF), and then, a mixture of 6.2 g of ethyl 6-hydrazinohexanoate hydrochloride, 7.42 g of triethylamine and 100 ml of DMF was added dropwise to the above mixture at room temperature. The resulting mixture was stirred at room temperature for 5 hours. DMF was removed under reduced pressure, and ethyl acetate was added to the residue. The mixture was washed and dried, and the solvent was removed under reduced pressure. The residue was applied to silica gel column chromatography (solvent; hexane:ethyl acetate=2:1) to give 5.8 g of {2-[3-(5-ethoxycarbonylpentyl)-3-aminoureido]-4-methoxy-6-tert-butylphenoxy}methoxymethane (state: oily product, IR: 3360, 1735, 1675, 1600 cm$^{-1}$) and 2.19 g of {2-[3-(5-ethoxycarbonylpentyl)-3-[3-(2-methoxymethoxy-3-tert-butyl-5-methoxyphenyl)ureido]ureido]-4-methoxy-6-tert-butylphenoxy}methoxymethane (state: oily product, IR: 3350, 1735, 1690, 1610, 1590 cm$^{-1}$), respectively.

(4) A mixture of 5 g of {2-[3-(5-ethoxycarbonylpentyl)-3-aminoureido]-4-methoxy-6-tert-butylphenoxy}methoxymethane, 5 g of 4-chlorobenzenesulfonyl chloride, 7.24 g of triethylamine and 20 ml of chloroform was refluxed for 4 hours. The solvent was removed under reduced pressure. Ethyl acetate was added to the residue and the mixture was washed and dried, and the solvent was removed under reduced pressure to give 4 g of {2-[3-(5-ethoxycarbonylpentyl)-3-(4-chlorobenzenesulfonylamino)ureido]-4-methoxy-6-tert-butylphenoxy}methoxymethane (yield: 57%, state: oily product, IR (film): 3400, 1732, 1710, 1610, 1590 cm$^{-1}$).

(5) The product (1.38 g) thus obtained was dissolved in 13 ml of tetrahydrofuran (THF), and 1.3 ml of conc. hydrochloric acid was added to the solution and the mixture was stirred at room temperature for 3 hours. The solvent was removed under reduced pressure. Ethyl acetate was added to the residue and the mixture was washed and dried, and then, the solvent was removed under reduced pressure. The residue was purified by silica gel column chromatography (solvent; chloroform:ethyl acetate=4:1) and crystallized from isopropyl ether to give 1.1 g of 2-[3-(5-ethoxycarbonylpentyl)-3-(4-chlorobenzenesulfonylamino)ureido]-4-methoxy-6-tert-butylphenol (yield: 86%, melting point: 69°–70° C).

Example 136

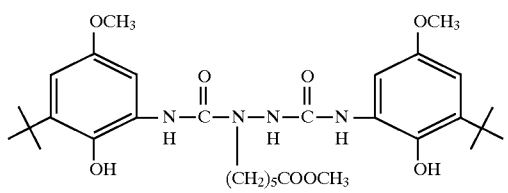

(1) A mixture of 2.2 g of {2-[3-(5-ethoxycarbonylpentyl)-3-[3-(2-methoxymethoxy-3-tert-butyl-5-methoxyphenyl)-ureido]ureido-4-methoxy-6-tert-butylphenoxy}methoxymethane obtained in Example 135 (3), 420 mg of 85% potassium hydroxide and 15 ml of methanol was stirred at room temperature for 3 hours. After removing methanol under reduced pressure, water and ethyl acetate was added to the residue and the mixture was acidified with 5% hydrochloric acid. The organic layer was separated, and washed and dried. After removing the solvent under reduced pressure, the residue was purified by silica gel column chromatography (solvent; chloroform:ethyl acetate= 5:1) to give 1.38 g of {2-[3-(5-methoxycarbonylpentyl)-3-[3-(2-methoxymethoxy-3-tert-butyl-5-methoxyphenyl)ureido]ureido-4-methoxy-6-tert-butylphenoxy}methoxymethane (yield: 64%, state: oily product, IR: 3350, 1740, 1690, 1610, 1590 cm$^{-1}$).

(2) The product (1.3 g) thus obtained was treated in the same manner as described in Example 135 (5) to give 650 mg of 2-[3-(5-methoxycarbonylpentyl)-3-[3-(2-hydroxy-3-tert-butyl-5-methoxyphenyl)ureido]ureido-4-methoxy-6-tert-butylphenol (yield: 57%, melting point: 157°–159° C.).

Example 137

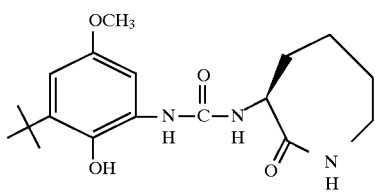

10% Palladium-carbon (Pd-C) (150 mg) was added to 10 ml of a methanol solution containing 500 mg of 2-[3-((1S)-5-benzyloxycarbonylamino-1-methoxycarbonylpentyl)ureido]-4-methoxy-6-tert-butylphenol. The mixture was subjected to catalytic reduction at normal pressure for 2 hours. After removing the catalyst, the reaction mixture was condensed. Methanol was added to the precipitated crystals and the crystals were collected by filtration to give 145 mg of 2-[3-((3S)-2-oxo-perhydroazepin-3-yl)ureido]-4-methoxy-6-tert-butylphenol (yield: 43%, melting point: 178°–179° C.).

Example 138

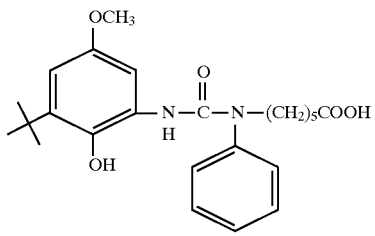

(1) A mixed solution of 47.9 ml of 2.901M phosgene-dichloromethane solution and 400 ml of dichloromethane was cooled to −78° C. To the mixture was added dropwise a mixture of 22.15 g of (2-amino-4-methoxy-6-tert-butylphenoxy)methoxymethane, 38.7 ml of triethylamine and 400 ml of dichloromethane. The temperature of the mixture was raised to 0° C., and the solvent was removed under reduced pressure. Dichloromethane (350 ml) was added to the residue, and at room temperature, a mixture of 21.78 g of N-phenyl-N-(5-ethoxycarbonylpentyl)amine, 19.4 ml of triethylamine and 350 ml of dichloromethane was added dropwise. The mixture was further stirred at room temperature overnight. The reaction mixture was washed and dried, the solvent was removed under reduced pressure and the residue was purified by silica gel column chromatography (solvent; chloroform:ethyl acetate=20:1) to give 27.72 g of {2-[3-phenyl-3-(5-ethoxycarbonylpentyl)ureido]-4-methoxy-6-tert-butylphenoxy}methoxymethane (yield: 60%, state: oily product, IR: 3380, 1735, 1680, 1610, 1595 cm$^{-1}$).

(2) A 10% sodium hydroxide aqueous solution (55 ml) was added to 275 ml of an ethanol solution containing 27.54 g of the product thus obtained, and the mixture was stirred at room temperature for 4 hours. Under ice-cooling, the reaction mixture was adjusted to pH=1 with 10% hydrochloric acid, and the mixture was extracted with ethyl acetate. The extract was washed and dried, and the solvent was removed under reduced pressure. The crystalline residue was recrystallized from a mixed solution of isopropyl ether and ethyl acetate to give 19.85 g of {2-[3-phenyl-3-(5-carboxypentyl)ureido]-4-methoxy-6-tert-butylphenoxy}methoxymethane (yield: 76%, melting point: 109°–111° C.).

(3) Conc. hydrochloric acid (4 ml) was added to 100 ml of a tetrahydrofuran (THF) solution containing 10.0 g of the product thus obtained, and the mixture was stirred at room temperature for one hour. The solvent was removed under reduced pressure, water was added to the residue and the mixture was extracted with ethyl acetate. The extract was washed and dried, and the solvent was removed under reduced pressure and the residue was recrystallized from a mixed solution of isopropyl ether and hexane to give 6.39 g of 2-[3-phenyl-3-(5-carboxypentyl)ureido]-4-methoxy-6-tert-butylphenol (yield: 70%, melting point: 95°–98° C.).

Examples 139 to 154

The corresponding starting materials were treated in the same manner as described in Example 138 to give the compounds as shown in Table 19.

TABLE 19

[Structure: phenol ring with OMe, OH, tert-butyl substituents, bearing N(H)-C(=O)-N(R$^5$)-R$^6$ group]

| Example | -R$^5$ | -R$^6$ | Melting point (°C.), etc. |
|---|---|---|---|
| 139 | pyridin-3-yl | -(CH$_2$)$_5$COOH | 133–134 |
| 140 | phenyl | -(CH$_2$)$_3$COOH | 118–120 |
| 141 | -CH$_2$-pyridin-3-yl | -(CH$_2$)$_5$COOH | 100–103 |
| 142 | phenyl | -(CH$_2$)$_6$COOH | 86–89 |
| 143 | pyridin-3-yl | -(CH$_2$)$_6$COOH | 131–134 |
| 144 | pyridin-3-yl | -(CH$_2$)$_4$COOH | 139–140 |
| 145 | phenyl | -(CH$_2$)$_4$COOH | 132–133 |
| 146 | -(CH$_2$)$_{15}$CH$_3$ | -C$_6$H$_4$-COOH | 129–131 |

TABLE 19-continued

| Example | -R⁵ | -R⁶ | Melting point (°C.), etc. |
|---|---|---|---|
| 147 | $-(CH_2)_{13}CH_3$ | -C₆H₄-COOH (para) | 132–134 |
| 148 | $-(CH_2)_7CH_3$ | -C₆H₄-COOH (para) | 151–152 |
| 149 | phenyl | $-CH_2COOH$ | 156–158 |
| 150 | cycloheptyl | $-(CH_2)_3COOH$ | Powder IR: 3310, 2931, 1708, 1620 (cm⁻¹) |
| 151 | 4-(CH₂)₇CH₃-phenyl | $-CH_2COOH$ | 129–131 |
| 152 | $-CH_2$-phenyl (benzyl) | $-(CH_2)_3COOH$ | Powder IR: 1708, 1628, 1530, 1490 (cm⁻¹) |
| 153 | 4-NMe₂-phenyl | $-CH_2COOH$ | 175–177 |
| 154 | $-H$ | -CH(CH₂Ph)COOH (S) | Powder IR: 3377, 1650, 1543 (cm⁻¹) |

Example 155

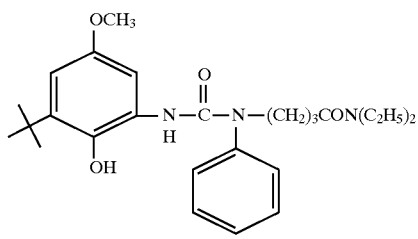

(1) Under ice-cooling, 2.5 g of 1,3-dicyclohexylcarbodiimide (DCC) was added to a mixture of 5.0 g of {2-[3-phenyl-3-(3-carboxypropyl)ureido]-4-methoxy-6-tert-butyl-phenoxy}methoxymethane, 1.4 g of N-hydroxysuccinimide (HOSu) and 50 ml of tetrahydrofuran (THF). The mixture was stirred at room temperature for 5 hours. Insoluble materials were filtered off and the filtrate was condensed. Under ice-cooling, a mixed solution of 1.2 ml of diethylamine and 10 ml of dimethylformamide (DMF) was added dropwise to a mixture of the obtained residue, 1.9 ml of tri-ethylamine and 10 ml of DMF. The resulting mixture was stirred at room temperature overnight. Ethyl acetate was added to the reaction mixture and the mixture was washed and dried, the solvent was removed under reduced pressure and the residue was purified by silica gel column chromatography (solvent; chloroform:ethyl acetate= 1:2) to give 3.95 g of {2-[3-phenyl-3-(3-diethylaminocarbonylpropyl)ureido]-4-methoxy-6-tertbutylphenoxy}methoxymethane (yield: 70%, state: pale yellow oily product, IR: 3340, 1676, 1635, 1590, 1519 cm$^{-1}$).

(2) Conc. hydrochloric acid (2 ml) was added to 30 ml of a THF solution containing 3.9 g of the product thus obtained, and the mixture was stirred at room temperature for one hour. After removing THF under reduced pressure, ethyl acetate was added to the residue and the mixture was washed and dried. The solvent was removed under reduced pressure and the residue was recrystallized from a mixed solution of isopropyl ether and ethyl acetate to give 2.86 g of 2-[3-phenyl-3-(3-diethylaminocarbonylpropyl)ureido]-4-methoxy-6-tert-butylphenol (yield: 80%, melting point: 131°–133° C.).

Examples 156 to 158

The corresponding starting materials were treated in the same manner as described in Example 155 to give the compounds as shown in Table 20.

TABLE 20

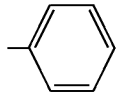

| Example | –R$^5$ | –R$^6$ | Melting point (°C.) |
|---|---|---|---|
| 156 | phenyl | –(CH$_2$)$_3$–C(=O)–NH–CH$_2$CH$_3$ | 156–158 |
| 157 | phenyl | –(CH$_2$)$_3$–C(=O)–NH–CH$_2$CHCH$_2$OH with OH | 102–105 |
| 158 | phenyl | –(CH$_2$)$_3$–C(=O)–N(morpholino) | 129–131 |

Example 159

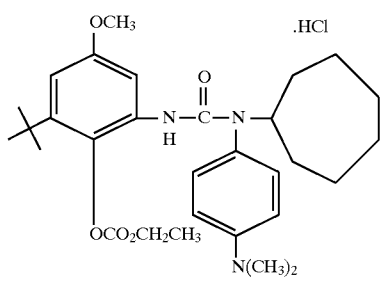

Under ice-cooling, 1.03 ml of ethyl chlorocarbonate was added dropwise to a mixed solution of 2.45 g of 2-[3-cycloheptyl-3-(4-dimethylaminophenyl)ureido]-4-methoxy-6-tertbutylphenol, 1.51 ml of triethylamine and 50 ml of dichloromethane, and the mixture was stirred at room temperature for 2 hours. After washing and drying, the solvent was removed under reduced pressure and the residue was purified by silica gel column chromatography (solvent; chloroform:ethyl acetate=20:1), and precipitated crystals were recrystallized from a mixed solution of isopropyl ether and ethyl acetate. The resulting crystals were dissolved in 50 ml of dichloromethane, and 2 ml of a 4N hydrogen chloride-dioxane solution was added thereto. The mixture was evaporated to dryness under reduced pressure. The residue was crystallized from an isopropyl ether solution to give 1.34 g of O-ethoxycarbonyl-2-[3-cycloheptyl-3-(4-dimethylaminophenyl)ureido]-4-methoxy-6-tert-butylphenol hydrochloride (yield: 44%, melting point: 163°–167° C. (decomposed)).

Example 160

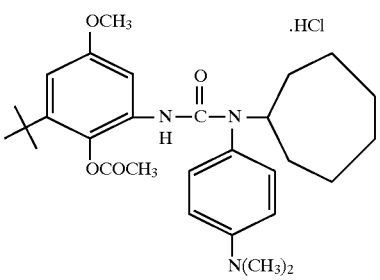

2-[3-Cycloheptyl-3-(4-dimethylaminophenyl)ureido]-4-methoxy-6-tert-butylphenol and acetic anhydride were treated in the same manner as described in Example 159 to give O-acetyl-2-[3-cycloheptyl-3-(4-dimethylaminophenyl) ureido]-4-methoxy-6-tert-butylphenol hydrochloride (melting point: 170°–171° C.).

Example 161

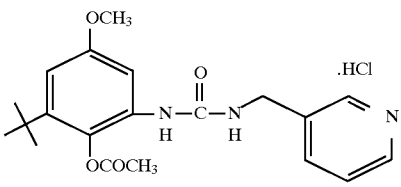

2-[3-(3-Pyridylmethyl)ureido]-4-methoxy-6-tert-butylphenol and acetic anhydride were treated in the same manner as described in Example 159 to give O-acetyl-2-[3-(3-pyridylmethyl)ureido]-4-methoxy-6-tert-butylphenol hydrochloride (melting point: 138°–142° C.).

Examples 162 to 166

The corresponding starting materials were treated in the same manner as described in Example 159 to give the compounds as shown in Table 21.

TABLE 21

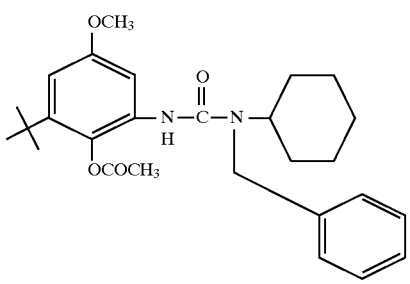

| Example | —R³ | Melting point (°C.) |
|---|---|---|
| 162 | —C(=O)—C₆H₅ | 201–203 |
| 163 | —C(=O)—cyclohexyl | 183–185 |
| 164 | —C(=O)—C(CH₃)₃ | 209–211 |
| 165 | —C(=O)—CH₂CH(CH₃)₂ | 145–147 |
| 166 | —C(=O)—CH₃ | 159–160 |

Examples 167 to 168

The corresponding starting materials were treated in the same manner as described in Example 159 to give the compounds as shown in Table 22.

TABLE 22

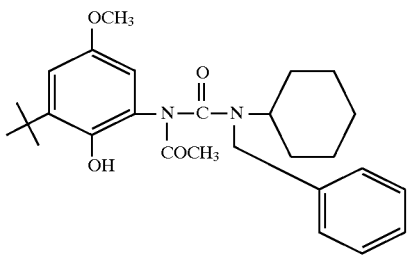

| Example | —R³ | Melting point (°C.), etc. |
|---|---|---|
| 167 | —C(=O)—OCH₂CH₃ | Powder IR: 3433, 1760, 1670 (cm⁻¹) |
| 168 | —C(=O)—C₆H₅ | 118–122 |

Example 169

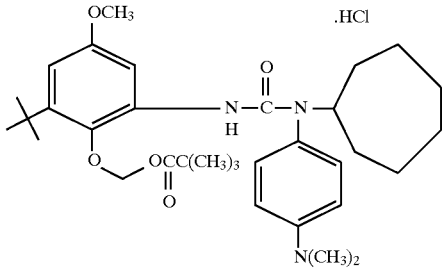

A mixture of 4.00 g of 2-(3-cyclohexyl-3-phenylmethylureido)-4-methoxy-6-tert-butylphenol, 2.0 ml of acetic anhydride, 3.2 ml of triethylamine and 80 ml of dichloromethane was stirred at room temperature for 24 hours. The reaction mixture was washed and dried, and the solvent was removed under reduced pressure. The residue was applied to silica gel column chromatography (solvent; chloroform:ethyl acetate=9:1) to give 735 mg of O-acetyl-2-(3-cyclohexyl-3-phenylmethylureido)-4-methoxy-6-tert-butylphenol (Rf=0.75, melting point: 129°–132° C. (recrystallized from hexane)).

Example 170

By continuing separation using silica gel column chromatography of Example 169, 2.53 g of 2-(1-acetyl-3-cyclohexyl-3-phenylmethylureido)-4-methoxy-6-tert-butylphenol was obtained. (Rf=0.39, melting point: 153°–155° C. (recrystallized from a mixed solution of isopropyl ether and ethyl acetate)).

Example 171

Under ice-cooling, 0.407 g of 62.4% sodium hydride was added to a mixture of 4.00 g of 2-[3-cycloheptyl-3-(4-dimethylaminophenyl)ureido]-4-methoxy-6-tert-butylphenol, 1.9 ml of chloromethylpivalate and 40 ml of dimethylformamide (DMF), and the temperature of the mixture was gradually raised to room temperature. The mixture was further stirred at room temperature for 2 hours.

A saturated saline solution was added to the mixture and the mixture was extracted with ethyl acetate. The extract was washed and dried, and the solvent was removed under reduced pressure. The residue was purified by silica gel column chromatography (solvent; hexane:ethyl acetate=4:1) and precipitated crystals were recrystallized from an isopropyl ether solution. The obtained crystals were dissolved in 10 ml of dichloromethane, and 5 ml of 4N hydrogen chloridedioxane solution was added to the solution. The mixture was evaporated to dryness under reduced pressure. The residue was crystallized from a diethyl ether solution to give 1.65 g of O-pivaloyloxymethyl-2-[3-cycloheptyl-3-(4-dimethylaminophenyl)ureido]-4-methoxy-6-tert-butylphenol hydrochloride (melting point: 114°–118° C. (decomposed)).

Example 172

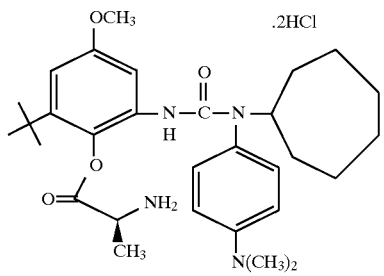

(1) A mixture of 1.5 g of 2-[3-cycloheptyl-3-(4-dimethylaminophenyl)ureido]-4-methoxy-6-tert-butylphenol, 2.16 g of N-benzyloxycarbonyl-L-alanine, 1.95 g of 1-ethyl-3-(3-dimethylaminopropyl)carbodiimide hydrochloride (WSC), 0.62 g of 4-dimethylaminopyridine (DMPA) and 30 ml of dimethylformamide (DMF) was stirred at room temperature for 5 hours. A saturated saline solution was added to the mixture and the mixture was extracted with ethyl acetate. The extract was washed and dried. The solvent was removed under reduced pressure and the residue was purified by silica gel column chromatography (solvent; hexane:ethyl acetate=4:1) to give 1.3 g of O-(N-benzyloxycarbonyl-L-alanyl)-2-[3-cycloheptyl-3-(4-dimethylaminophenyl)ureido]-4-methoxy-6-tert-butylphenol (yield: 60%, melting point: 126° C.).

(2) The product (800 mg) thus obtained was dissolved in 50 ml of methanol. 1 ml of conc. hydrochloric acid and 200 mg of 10% palladium-carbon (Pd-C) were added to the solution and the mixture was subjected to medium pressure catalytic reduction by using a Parr's reduction apparatus for one hour. After removing the catalyst by filtration, the filtrate was evaporated to dryness under reduced pressure, and to the residue was added diethyl ether to give 600 mg of O-(L-alanyl)-2-[3-cycloheptyl-3-(4-dimethylaminophenyl)ureido]-4-methoxy-6-tert-butylphenol dihydrochloride as powder (yield: 83%, IR: 3424, 1771, 1674, 1640, 1599 cm$^{-1}$).

Examples 173 to 177

The corresponding starting materials were treated in the same manner as described in Example 172 to give the compounds as shown in Table 23.

TABLE 23

| Example | –R³ | Properties |
|---|---|---|
| 173 | –C(=O)–CH₂NH₂ | Dihydrochloride Powder<br>IR: 3450, 1775, 1645, 1601, 1510 (cm⁻¹)<br>Dihydrochloride Powder |
| 174 | –C(=O)–CH(NH₂)–COOH | Dihydrochloride Powder<br>IR: 3453, 1772, 1733, 1635, 1601 (cm⁻¹) |
| 175 | –C(=O)–CH₂CH₂–CH(NH₂)–COOH | Dihydrochloride Powder<br>IR: 3420, 1745, 1634, 1601 (cm⁻¹) |
| 176 | –C(=O)–CH(NH₂)–(CH₂)₄–NH₂ | Trihydrochloride Powder<br>IR: 3421, 1767, 1633, 1602 (cm⁻¹) |
| 177 | –C(=O)–CH(NH₂)–CH(CH₃)₂ | Dihydrochloride Powder<br>IR: 3420, 1764, 1650, 1599 (cm⁻¹) |

Example 178

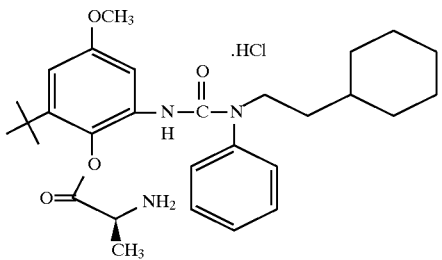

(1) A mixture of 2.45 g of 2-[3-(2-cyclohexylethyl)-3-phenylureido]-4-methoxy-6-tert-butylphenol, 10.30 g of N-benzyloxycarbonyl-L-alanine, 8.81 g of 1-ethyl-3-(3-dimethylaminopropyl)carbodiimide hydrochloride (WSC), 1.06 g of 4-dimethylaminopyridine (DMPA) and 50 ml of DMF was stirred at room temperature for 4 hours. Then, a saturated saline solution was added to the mixture and the mixture was extracted with ethyl acetate, and the extract was washed and dried. The solvent was removed under reduced pressure and the residue was purified by silica gel column chromatography (solvent; hexane:ethyl acetate=2:1) to separate 1.09 g of O-(N-benzyloxycarbonyl-L-alanyl)-2-[3-(2- cyclohexylethyl)-3-phenylureido]-4-methoxy-6-tert-butylphenol (Compound A) (Rf=0.71, yield: 30%, state: oily product, IR (film): 3325, 1726 cm⁻¹) and 1.89 g of 2-[1-(N-benzyloxycarbonyl-L-alanyl)-3-(2-cyclohexylethyl)-3-phenylureido]-4-methoxy-6-tert-butylphenol (Compound B) (Rf=0.39, yield: 52%, state: oily product, IR (film): 3319, 1710 cm⁻¹).

(2) To 40 ml of a methanol solution containing 1.70 g of Compound A obtained in (1) were added 1 ml of conc. hydrochloric acid and 0.75 g of 10% palladium-carbon (Pd-C). The mixture was subjected to catalytic reduction at normal temperature under normal pressure for 2 hours. After removing the catalyst by filtration, the filtrate was evaporated to dryness under reduced pressure. The residue was crystallized by adding hexane to give 1.29 g of O-(L-alanyl)-2-[3-(2-cyclohexylethyl)-3-phenylureido]-4-methoxy-6-tert-butylphenol (yield: 90%, state: oily product, IR: 3420, 1775, 1750, 1675, 1650, 1595 cm⁻¹).

Example 179

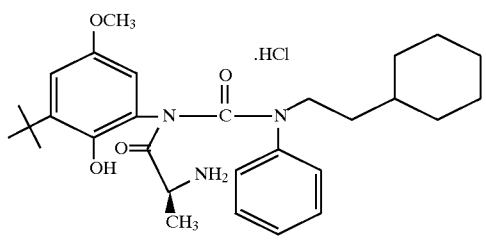

To 75 ml of a methanol solution containing 2.5 g of Compound B obtained in Example 178 (1) were added 1.5 ml of conc. hydrochloric acid and 1.0 g of 10% palladium-carbon (Pd-C). The mixture was subjected to catalytic reduction at normal temperature under normal pressure for 2 hours. After removing the catalyst by filtration, the filtrate was evaporated to dryness under reduced pressure, and the residue was crystallized by adding hexane to give 1.80 g of 2-[1-L-alanyl-3-(2-cyclohexylethyl)-3-phenylureido]-4-methoxy-6-tert-butylphenol (yield: 85%, state: powder, IR: 3500 (br), 1730, 1705 cm⁻¹).

Examples 180 and 181

2-[3-(2-Cyclohexylethyl)-3-phenylureido]-4-methoxy-6-tert-butylphenol, N-benzyloxycarbonylglycine and others were treated in the same manner as described in Examples 178 arid 179 to give the following compounds.

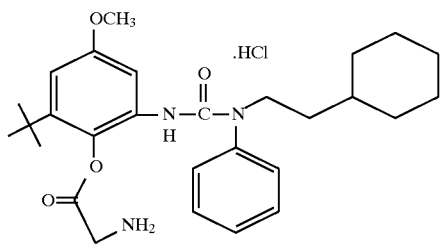

(Example 180)

O-Glycyl-2-[3-(2-cyclohexylethyl)-3-phenylureido]-4-methoxy-6-tert-butylphenol hydrochloride IR: 3450, 1778, 1690, 1594 cm⁻¹

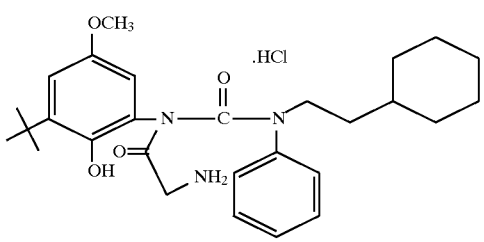

(Example 181)

2-[1-Glycyl-3-(2-cyclohexylethyl)-3-phenylureido]-4-methoxy-6-tert-butylphenol hydrochloride IR: 3480 (br), 1699, 1596 cm⁻¹

Example 182

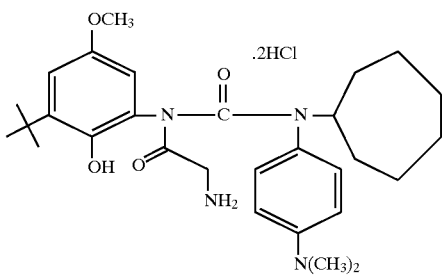

(1) 2-[3-Cycloheptyl-3-(4-dimethylaminophenyl)ureido]-4-methoxy-6-tert-butylphenol and N-benzyloxycarbonylglycine were treated in the same manner as described in Example 172 (1) to give O-(N-benzyloxycarbonylglycyl)-2-[3-cycloheptyl-3-(4-dimethylaminophenyl)ureido]-4-methoxy-6-tert-butylphenol.

(2) Triethylamine (0.42 ml) was added to a 6 ml of DMF solution containing 646 mg of the product thus obtained, and the mixture was stirred at room temperature overnight. Water was added to the mixture, and the mixture was extracted with ethyl acetate. The extract was washed and dried, and the solvent was removed under reduced pressure. To 30 ml of a methanol solution containing the thus obtained residue were added 0.3 ml of conc. hydrochloric acid and 100 mg of 10% palladium-carbon (Pd-C). The mixture was subjected to catalytic reduction by using a Parr's reduction apparatus for one hour. After removing the catalyst by filtration, the filtrate was evaporated to dryness under reduced pressure. Diethyl ether was added to the residue to give 351 mg of 2-[1-glycyl-3-cycloheptyl-3-(4-dimethylaminophenyl)ureido]-4-methoxy-6-tert-butylphenol dihydrochloride as powder (yield: 60%, IR: 3450 (br), 1711, 1607, 1511 cm⁻¹).

Example 183

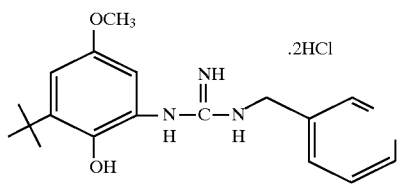

(1) A 10% sodium hydroxide aqueous solution (8.8 ml) was added to 2.16 g of 3-aminomethylpyridine, then, 1.8 ml of carbon disulfide was added dropwise to the mixture at room temperature and the mixture was stirred at room temperature for one hour. Under ice-cooling, 2.39 g of ethyl chlorocarbonate was added dropwise to the mixture and the resulting mixture was stirred at room temperature for one hour. Water was added to the mixture, and the mixture was extracted with ethyl acetate. The extract was washed and dried, and the solvent was removed under reduced pressure. To the obtained residue were added 4.79 g of 2-amino-4-methoxy-6-tert-butylphenoxy)methoxymethane and 20 ml of toluene. After refluxing the mixture for one hour, water was added to the mixture and the mixture was extracted with ethyl acetate. The extract was washed and dried, and the solvent was removed under reduced pressure. The residue was purified by silica gel column chromatography (solvent; ethyl acetate) and recrystallized from a mixed solution of isopropyl ether and ethyl acetate to give 3.85 g of {2-[3-(3-pyridylmethyl)thioureido]-4-methoxy-6-tert-butylphenoxy}methoxymethane (yield: 49%, melting point: 137°–138° C.).

(2) A mixture of 2.5 g of the product thus obtained, 50 ml of 14.5% ammonia-methanol solution and 2.5 g of copper sulfate pentahydrate was vigorously stirred at 40° C. for 3 hours. Insoluble materials were removed from the mixture by filtration, and after condensing the filtrate, the residue was purified by silica gel column chromatography (solvent; chloroform:ethanol=2:1) to give 2.11 g of {2-[3-(3-pyridylmethylguanidino]-4-methoxy-6-tert-butylphenoxy}methoxymethane (yield: 88%, melting point: 103°–108° C.).

(3) After stirring a mixture of 2.07 g of the product thus obtained, 3 ml of conc. hydrochloric acid and 35 ml of methanol at room temperature for 2 hours, the mixture was evaporated to dryness under reduced pressure. The residue was crystallized from an ethyl acetate solution. The crystals were further recrystallized from a mixed solution of ethyl acetate and ethanol to give 1.90 g of 2-[3-(3-pyridylmethyl)guanidino]-4-methoxy-6-tert-butylphenol dihydrochloride (yield: 85%, melting point: 160°–165° C.).

Example 184

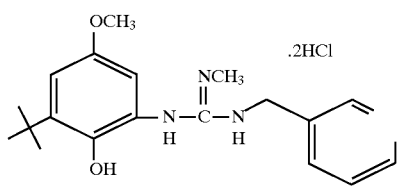

(1) {2-[3-(3-Pyridylmethyl)thioureido]-4-methoxy-6-tert-butylphenoxy}methoxymethane and methylamine were treated in the same manner as described in Example 183 (2) to give {2-[2-methyl-3-(3-pyridylmethyl)guanidino]-4-methoxy-6-tert-butyldhenoxy}methoxymethane as oily product.

(2) The product thus obtained was treated in the same manner as described in Example 183 (3) to give 2-[2-methyl-3-(3-pyridylmethyl)guanidino]-4-methoxy-6-tert-butylphenol dihydrochloride (melting point: 158°–161° C.).

Example 185

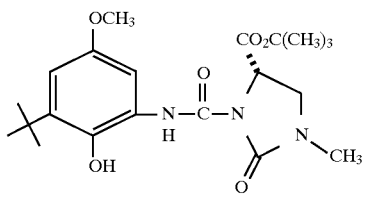

(1) A dichloromethane (170 ml) solution containing 2.97 g of triphosgene was cooled to −78° C., and a mixture of 5.98 g of (2-amino-4-methoxy-6-tert-butylphenoxy) methoxymethane, 6.97 ml of triethylamine and 80 ml of dichloromethane was added dropwise to the solution. The temperature of the mixture was raised to 0° C., and the solvent was removed under reduced pressure to give a residue.

On the other hand, 170 ml of a THF solution containing 5.00 g of tert-butyl (4S)-1-methyl-2-oxoimidazolidine-4-carboxylate was cooled to −78° C., and 2.95 g of potassium tert-butoxide was added to the solution. After raising the temperature to −30° C., the mixture was cooled again to −78° C., and 80 ml of a THF solution containing the residue obtained above was gradually poured to the mixture. The resulting mixture was stirred at the same temperature for 30 minutes, and the reaction mixture was added to a mixed solution of 150 ml of ethyl acetate, 1.5 ml of acetic acid and 150 ml of a saturated saline solution. The organic layer was separated and the remaining aqueous layer was extracted with ethyl acetate. The organic layer and the extract were combined. The mixture was washed and dried, and the solvent was removed under reduced pressure. The residue was recrystallized from an isopropyl ether solution to give 8.43 g of {2-[(4S)-2-oxo-1-methyl-4-tert-butoxycarbonylimidazolidin-3-ylamido]-4-methoxy-6-tert-butylphenoxy}methoxymethane (yield: 72%, melting point: 133°–134° C.).

(2) A mixture of 3.03 g of the product thus obtained, 0.5 ml of conc. hydrochloric acid and 60 ml of methanol was stirred at room temperature for 2 hours. The mixture was evaporated to dryness under reduced pressure and the residue was purified by silica gel column chromatography (solvent; hexane:ethyl acetate=1:1) and recrystallized from isopropyl ether to give 1.49 g of 2-[(4S)-2-oxo-1-methyl-4-tert-butoxycarbonylimidazolidin-3-ylamido]-4-methoxy-6-tert-butylphenol (yield: 54%, melting point: 123°–124° C.).

Example 186

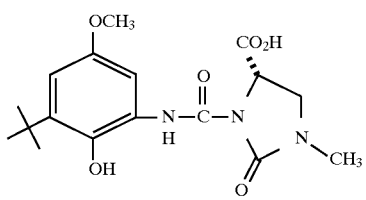

A mixture of 624 mg of the product obtained in Example 185 and 6 ml of trifluoroacetic acid was stirred at room temperature for one hour, and the mixture was evaporated to dryness under reduced pressure. Toluene was added to the residue and the mixture was again evaporated to dryness under reduced pressure, and the residue was crystallized from an isopropyl ether solution to give 258 mg of 2-[(4S)-2-oxo-1-methyl-4-carboxyimidazolidin-3-ylamido]-4-methoxy-6-tert-butylphenol (yield: 48%, melting point: 102°–104° C.).

Example 187

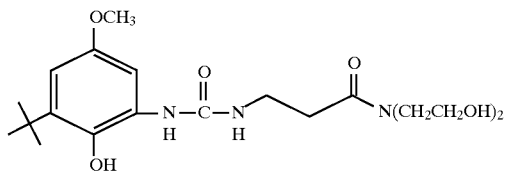

(1) Triethylamine (13.3 ml) was added dropwise to a mixture of 5 g of bis(2-hydroxyethyl)amine, 14.3 g of tert-butyl-dimethylsilyl chloride and 100 ml of dimethylformamide (DMF). A catalytic amount of 4-dimethylaminopyridine was added to the mixture and the resulting mixture was stirred for 5 hours. Then, the mixture was diluted with ethyl acetate. The diluted mixture was washed and dried, and the solvent was removed under reduced pressure. To the obtained residue were added 10.6 g of 3-(N-benzyloxycarbonylamino)-propionic acid, 7.1 g of 1-hydroxybenzotriazole and 100 ml of DMF, and under ice-cooling, 10.8 g of 1,3-dicyclohexylcarbodiimide (DCC) was added to the mixture. The resulting mixture was stirred at room temperature overnight. The mixture was diluted with ethyl acetate, and insoluble materials were removed from the mixture by filtration. The filtrate was washed and dried, and the solvent was removed under reduced pressure. The residue was applied to silica gel column chromatography (solvent; hexane:ethyl acetate=4:1). The condensed eluate was dissolved in 200 ml of methanol, and 1 g of 10% palladium-carbon (Pd-C) was added to the solution. The mixture was subjected to catalytic reduction at normal temperature under normal pressure for 0.5 hour. The catalyst was filtered off, and the filtrate was condensed to give 11.4 g of {2-[bis(2-tert-butyldimethylsilyloxyethyl)amino]carbonylethyl}amine (yield: 59%) as a colorless oily product.

(2) The product thus obtained was treated in the same manner as described in Example 16 (1) to give {2-[3-[2-[bis(2-tert-butyldimethylsilyloxyethyl)aminocarbonyl]ethyl]ureido]-4-methoxy-6-tert-butylphenoxy}methoxymethane (yield: 71%, IR (film): 3361, 1648 cm$^{-1}$).

(3) To a mixed solution of 3.196 g of the product thus obtained and 50 ml of THF was added 14 ml of a THF solution containing 1M tetrabutylammonium fluoride, and the mixture was stirred at room temperature for one hour. THF was removed under reduced pressure and ethyl acetate was added to the residue. The mixture was washed and dried, and then the solvent was removed under reduced pressure. The residue was purified by silica gel column chromatography (solvent; chloroform:methanol=9:1) to give 0.926 g of {2-[3-[2-[bis(2-hydroxyethyl)aminocarbonyl]ethyl]ureido]-4-methoxy-6-tert-butylphenoxy}methoxymethane (yield: 44%, IR (KBr): 3407, 1676, 1614 cm$^{-1}$ (4) A mixture of 843 mg of the product thus obtained, 0.5 ml of conc. hydrochloric acid and 10 ml of methanol was stirred at room temperature for one hour. Methanol was removed under reduced pressure, ethyl acetate was added to the residue and the mixture was washed and dried. The solvent was removed under reduced pressure and the residue was purified by silica gel column chromatography (solvent; chloroform:methanol=9:1) to give 385 mg of 2-{3-[2-[bis(2-hydroxyethyl)aminocarbonyl]ethyl]ureido}-4-methoxy-6-tert-butylphenol (yield: 51%, IR (film): 3344, 1615 cm$^{-1}$).

Example 188

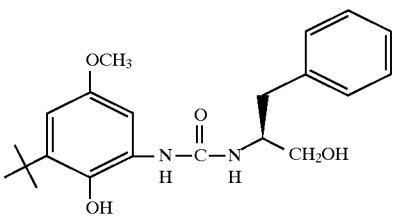

(1) (2-Amino-4-methoxy-6-tert-butylphenoxy)methoxymethane, phosgene and L-phenylalanine methyl ester were treated in the same manner as described in Example 16 (1) to give {2-[3-((1S)-1-methoxycarbonyl-2-phenylethyl)ureido]-4-methoxy-6-tert-butylphenoxy}methoxymethane.

(2) To a refluxed solution of 4.00 g of the product thus obtained, 851 mg of sodium borohydride and 48 ml of THF was gradually added dropwise a mixture of 7.2 ml of methanol and 8 ml of THF. The mixture was further refluxed for one hour. After cooling, water was added and the mixture was extracted with dichloromethane. The extract was washed and dried. The solvent was removed under reduced pressure and the residue was purified by silica gel column chromatography (solvent; ethyl acetate) to give 3.674 g of {2-[3-((1S)-1-hydroxymethyl-2-phenylethyl)ureido]-4-methoxy-6-tert-butylphenoxy}methoxymethane (yield: 98%, IR: 3350, 1650, 1551 cm$^{-1}$).

(3) The product thus obtained was treated in the same manner as described in Example 16 (2) to give 2-[3-((1S)-1-hydroxymethyl-2-phenylethyl)ureido]-4-methoxy-6-tert-butylphenol (IR: 3356, 1645, 1558 cm$^{-1}$).

Example 189

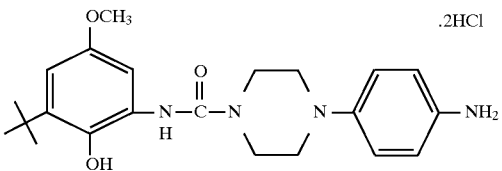

To a mixture of 680 mg of 2-{[4-(4-nitrophenyl)piperazin-1-yl]carbonylamino}-4-methoxy-6-tert-butylphenol hydrochloride, 30 ml of methanol and 30 ml of dioxane was added 100 mg of 10% palladium-carbon (Pd-C). The mixture was subjected to catalytic reduction for 4 hours by using a Parr's reduction apparatus. After removing the catalyst by filtration, the filtrate was condensed. The residue was dissolved in 10 ml of dichloromethane, and after adding 1 ml of 4N hydrogen chloride-dioxane solution, the mixture was treated with an activated charcoal. The treated mixture was evaporated to dryness under reduced pressure to give 210 mg of 2-{[4-(4-aminophenyl)piperazin-1-yl]carbonylamino}-4-methoxy-6-tert-butylphenol dihydrochloride as powder.

Example 190

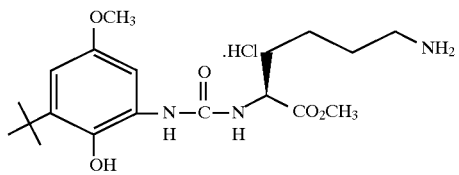

To a mixed solution comprising 1 g of 2-[3-((1S)-5-benzyloxycarbonylamino-1-methoxycarbonylpentyl)ureido]-4-methoxy-6-tert-butylphenol and 30 ml of methanol were added 0.5 ml of conc. hydrochloric acid and 200 mg of 10% palladium-carbon (Pd-C). The mixture was subjected to catalytic reduction at normal temperature under normal pressure for one hour. After removing the catalyst, the filtrate was condensed. Hexane was added to the residue to give 685 mg of 2-[3-((1S)-5-amino-1-methoxycarbonylpentyl)ureido]-4-methoxy-6-tert-butylphenol hydrochloride (yield: 85%, state: yellow powder, IR: 3300 (br), 1725, 1650, 1560 cm$^{-1}$).

Example 191

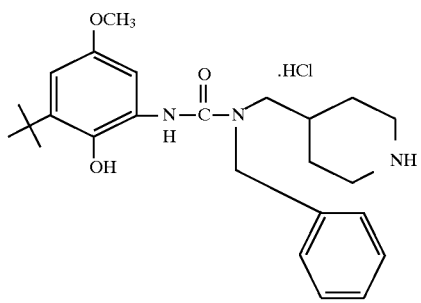

4N hydrogen chloride-dioxane solution (15 ml) was added to 1.50 g of 2-[3-(1-tert-butoxycarbonylpiperidin-4-yl)methyl-3-phenylmethylureido]-4-methoxy-6-tert-butylphenol, and the mixture was stirred at room temperature for 2 hours. Then, the mixture was evaporated to dryness under reduced pressure and the residue was recrystallized from an ethanol solution to give 0.912 g of 2-[3-(4-piperidylmethyl)-3-phenylmethylureido]-4-methoxy-6-tert-butylphenol hydrochloride (yield: 69%, melting point: 195°–196° C.).

Example 192

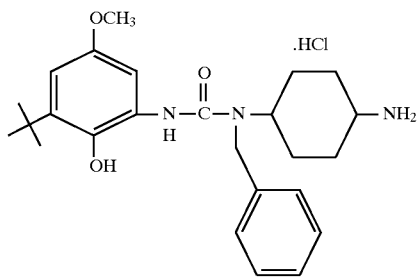

2-[3-(4-tert-Butoxycarbonylaminocyclohexyl)-3-phenylmethylureido]-4-methoxy-6-tert-butylphenol was treated in the same manner as described in Example 191 to give 2-[3-(4-aminocyclohexyl)-3-phenylmethylureido]-4-methoxy-6-tert-butylphenol hydrochloride (IR: 3400, 1626 cm$^{-1}$).

Example 193

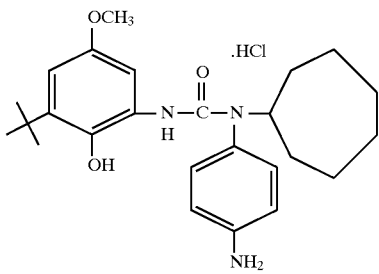

2-[3-(4-tert-Butoxycarbonylaminophenyl)-3-cycloheptylureido]-4-methoxy-6-tert-butylphenol was treated in the same manner as described in Example 191 to give 2-[3-(4-aminophenyl)-3-cycloheptylureido]-4-methoxy-6-tert-butylphenol hydrochloride (melting point: 156°–157° C.).

Example 194

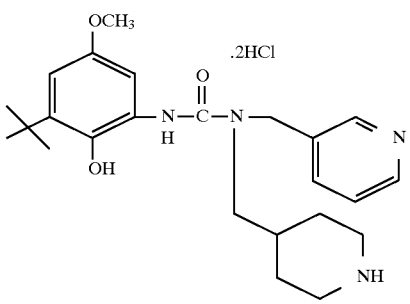

2-[3-(1-tert-Butoxycarbonylpiperidin-4-ylmethyl)-3-(3-pyridylmethyl)ureido]-4-methoxy-6-tert-butylphenol was treated in the same manner as described in Example 191 to give 2-[3-(4-piperidylmethyl)-3-(3-pyridylmethyl)ureido]-4-methoxy-6-tert-butylphenol dihydrochloride (IR: 3418, 1630, 1530, 1471 cm$^{-1}$).

Example 195

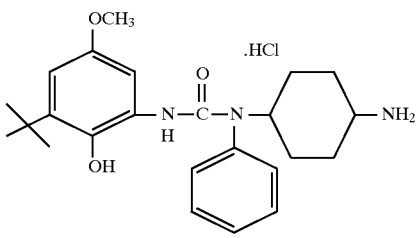

(1) (2-Amino-4-methoxy-6-tert-butylphenoxy)methoxymethane, N-phenyl-N-(4-benzyloxycarbonylaminocyclohexyl)amine and triphosgene were treated in the same manner as described in Example 53 to give {2-[3-phenyl-3-(4-benzyloxycarbonylaminocyclohexyl)ureido]-4-methoxy-6-tert-butylphenoxy}methoxymethane (melting point: 145°–154° C.).

(2) To a mixed solution comprising 2.192 g of the product thus obtained and 300 ml of methanol was added 1 g of 10% palladium-carbon (Pd-C). The mixture was subjected to catalytic reduction at normal temperature under normal pressure for 3 hours. After removing the catalyst by filtration, the filtrate was condensed to give {2-[3-phenyl-3-(4-aminocyclohexyl)ureido]-4-methoxy-6-tert-butylphenoxy}methoxymethane (yield: 98%, IR: 3400, 1667, 1594, 1519 cm$^{-1}$).

(3) The product thus obtained was treated in the same manner as described in Example 53 (2) to give 2-[3-phenyl-3-(4-aminocyclohexyl)ureido]-4-methoxy-6-tert-butylphenol hydrochloride (state: powder, IR: 3390, 1636, 1520 cm$^{-1}$).

Examples 196 to 256

The corresponding starting materials are treated in the same manner as described in any of the above-mentioned Examples to give the compounds as shown in Table 24.

TABLE 24

| Example | $-\underset{R^6}{\overset{R^5}{N}}-$ | Melting point (°C.), etc. |
|---|---|---|
| 196 | -NH-CH(CH₃)-(3-pyridyl) .HCl | Powder IR: 3264, 1655, 1610, 1559 (cm$^{-1}$) |
| 197 | -N(piperazinyl)-CH₂CH₂OH | Powder IR: 3356, 1629 (cm$^{-1}$) |
| 198 | -NH-CH₂-(6-methylpyridin-3-yl) .2HCl | 90–95 |
| 199 | -N(piperazinyl)-(pyrimidin-2-yl) .HCl | 137–140 |
| 200 | -NH-CH(2-pyridyl)₂ .2HCl | 174–176 |

TABLE 24-continued

| | | |
|---|---|---|
| 201 | 3-hydroxy-4-(methylaminomethyl)-5-(hydroxymethyl)-2-methylpyridine .HCl | 150–152 |
| 202 | -N(piperazinyl)-CH₂-(3-aminophenyl) | Dihydrochloride |
| 203 | -N(piperazinyl)-CH₂-(4-aminophenyl) | Dihydrochloride |
| 204 | -N(piperazinyl)-CH₂CH₂-(4-aminophenyl) | Dihydrochloride |
| 205 | -N(piperazinyl)-CH₂CH₂-(4-aminophenyl) | Dihydrochloride |
| 206 | -N(piperazinyl)-(3-pyridyl) | Dihydrochloride |
| 207 | -N(piperazinyl)-CH₂-(3-pyridyl) | Dihydrochloride |
| 208 | -N(piperazinyl)-CH₂-(4-pyridyl) | Dihydrochloride |
| 209 | -N(piperazinyl)-CH₂-(2-morpholinophenyl) | Dihydrochloride |
| 210 | -N(piperazinyl)-CH₂CH₂NH₂ | Dihydrochloride |
| 211 | -N(piperazinyl)-(indol-5-yl) | Dihydrochloride |

TABLE 24-continued

| # | Structure | Form/mp |
|---|---|---|
| 212 | [piperazine linked to benzene with fused imidazoline ring -NH] | Dihydrochloride |
| 213 | [N-methylpiperazine linked to 2,4-diaminobenzene] | Trihydrochloride |
| 214 | [N-methylpiperazine linked to pyrimidine bearing two pyrrolidinyl groups] | Trihydrochloride |
| 215 | [N-methylpiperidine-piperidine] | Hydrochloride |
| 216 | [N-methylpiperidine-phenyl-NH₂] | Hydrochloride |
| 217 | [N-methylpiperazine-phenyl-NH₂] | Dihydrochloride |
| 218 | [N-methyl diazocane-phenyl-NH₂] | Dihydrochloride |
| 219 | -N(Me)CH₂CH₂NH-C₆H₄-NH₂ | Dihydrochloride |
| 220 | -N(Me)CH₂CH₂NHCH₂CH₂NH₂ | Dihydrochloride |
| 221 | -N(H)Me-pyridine-2-NH₂ · HCl | 194–196 (decomped) |
| 222 | -N(H)Me-CH₂-pyridine-2-NH₂ · HCl | Powder IR: 3303, 1673, 1625, 1552 (cm⁻¹) |
| 223 | -N(H)Me-CH₂-(6-methylpyridin-3-yl) · HCl | 163–166 |
| 224 | -N(H)Me-CH₂-(6-methyl-2-oxo-1,2-dihydropyridin-3-yl) | 148–150 |
| 225 | -N(H)Me-CH₂-(1-methylpyridinium-3-yl) I⁻ | 176–177 |
| 226 | -N(Me)-CH₂-pyridin-3-yl with propyl-pyridin-3-yl · 2HCl | Powder IR: 3400, 1642, 1471 (cm⁻¹) |
| 227 | -N(Me)-CH₂CH₂-(4-aminocyclohexyl) with phenyl · HCl | 165–168 |
| 228 | -N(Me)-6-(1,2,3,4-tetrahydroquinolinyl) | Hydrochloride |
| 229 | -N(Me)-CH₂-(piperidine) linked to piperidine | Dihydrochloride |
| 230 | -N(Me)-bis(pyridin-3-yl) | Dihydrochloride |
| 231 | -N(H)Me-CH₂-(imidazol-4-yl) | Hydrochloride |

TABLE 24-continued

| | | |
|---|---|---|
| 232 | [structure: -N-CH2-N(HN=N)-CH2-NH-... bis-imidazole methylene] | Dihydrochloride |
| 233 | [structure: piperazine-N-(2-aminophenyl)] H2N | Dihydrochloride |
| 234 | [structure: piperazine-N-(3-aminophenyl)] NH2 | Dihydrochloride |
| 235 | [structure: piperazine-N-C6H4-N(CH3)2 (para)] | Dihydrochloride |
| 236 | [structure: piperazine-N-C6H4-OH (para)] | Hydrochloride |
| 237 | [structure: piperazine-N-phenyl] | Hydrochloride |
| 238 | [structure: piperazine-N-C6H4-C(=NH)NH2] | Dihydrochloride |
| 239 | [structure: piperazine-N-C6H4-N-piperazine] | Trihydrochloride |
| 240 | [structure: piperazine-N-C6H4-N-morpholine] | Dihydrochloride |

[Structure: 
OMe
    \
     C6H2(t-Bu)(OH)-N(R4)-C(=O)-N(R5)(R6)
]

| Example | -R4 | -N(R5)(R6) | Melting point (°C.), etc. |
|---|---|---|---|
| 241 | -CH3 | [-N(CH2-3-pyridyl)2] | Dihydrochloride |

TABLE 24-continued

| | | |
|---|---|---|
| 242 | -CH2-(3-pyridyl) | -NH-CH2-(3-pyridyl) | Dihydrochloride |

[Structure:
OMe
    \
     C6H2(t-Bu)(OH)-NH-C(=O)-N(R5)(R6)
]

| Example | -N(R5)(R6) | Melting point (°C.), etc. |
|---|---|---|
| 243 | [piperazine-N-C6H4-NHCH3 (para)] | Dihydrochloride |
| 244 | [piperazine-N-C6H4-NHCH3 (meta)] | Dihydrochloride |
| 245 | [piperazine-N-C6H4-NHCH3 (ortho)] | Dihydrochloride |
| 246 | [piperazine-N-C6H4-N(CH3)2 (meta)] | Dihydrochloride |
| 247 | [piperazine-N-C6H4-N(CH3)2 (ortho)] | Dihydrochloride |
| 248 | [piperazine-N-CH2-C6H4-NH2 (ortho)] | Dihydrochloride |
| 249 | [piperazine-N-CH2-C6H4-N(CH3)2 (meta)] | Dihydrochloride |
| 250 | [piperazine-N-CH2-C6H4-N(CH3)2 (para)] | Dihydrochloride |

TABLE 24-continued

| | | |
|---|---|---|
| 251 | ![structure] -N(piperazine)N=CH-C6H4-NH2 | Dihydrochloride |
| 252 | -NH-CH2CH2-NH-C6H4-N(CH3)2 | Dihydrochloride |
| 253 | -NH-CH2CH2-NH-(pyridyl)-NH2 | Dihydrochloride |
| 254 | -N(piperazine)N-CH2-C(=N-C6H4-NH-) | Dihydrochloride |
| 255 | -N(-CH2-pyridyl)-CH2CH2CH2-N-CH=N (imidazole) | Dihydrochloride |
| 256 | -N-CH2-C(=N-C6H4-NH-CH2CH2-N-CH=N(imidazole)) | Dihydrochloride |

Example 257

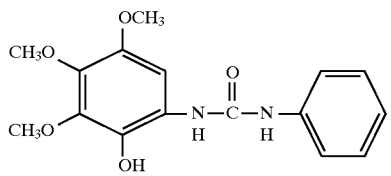

4,5,6-trimethoxyphenoxy)methoxymethane was treated in the same manner as described in Example 1 to give 2-(3-phenylureido)-4,5,6-trimethoxyphenol (melting point: 123°–125° C.).

Reference Example 1

(1) p-Anisidine (257 g) was dissolved in 514 ml of conc. hydrochloric acid, and under ice-cooling, 1530 ml of an aqueous solution containing 158 g of sodium nitrite was added dropwise to the solution. This mixture was added dropwise under ice-cooling to 3000 ml of an aqueous solution containing 356 g of 4-methoxy-2-tert-butylphenol and 416 g of sodium hydroxide. The resulting mixture was stirred at the same temperature for 15 minutes. Conc. hydrochloric acid (about 400 ml) was added dropwise to the reaction mixture to adjust pH of the mixture to 3, and the precipitated crystals were collected by filtration. The crystals were washed and dried, and recrystallized from a mixed solution of chloroform and ethanol to give 400 g of 2-(4-methoxyphenylazo)-4-methoxy-6-tert-butylphenol (yield: 64%, melting point: 125°–127° C., IR: 1600 cm$^{-1}$).

(2) To a suspension of 63 g of 62.5% sodium hydride and 2500 ml of dimethylformamide (DMF) was added dropwise under ice-cooling 3000 ml of a tetrahydrofuran (THF) solution containing 472 g of 2-(4-methoxyphenylazo)-4-methoxy-6-tert-butylphenol. After elevating the temperature to room temperature, the mixture was ice-cooled again, and 133 g of methoxymethyl chloride was added dropwise. After stirring at room temperature for 2 hours, 300 ml of an aqueous saturated ammonium chloride solution was gradually added dropwise to the mixture. THF was removed under reduced pressure, and a saturated saline solution was added to the residue. The mixture was extracted with ethyl acetate. The extract was washed and dried, and the solvent was removed under reduced pressure. The precipitated crystals were recrystallized from a mixed solution of hexane and ethyl acetate to give 520 g of [2-(4-methoxyphenylazo)-4-methoxy-6-tert-butylphenoxy]methoxymethane (yield: 97%, melting point: 102°–103° C., IR: 1610 cm$^{-1}$).

(3) To 1200 ml of a methanol solution containing 180 g of the product thus obtained was added 3 g of 10% palladium-carbon (Pd-C). The mixture was subjected to catalytic reduction at room temperature for 30 minutes by using a Parr's reduction apparatus. After removing the catalyst by filtration, the filtrate was evaporated to dryness under reduced pressure. The obtained residue was evaporated under reduced pressure to give 109 g of (2-amino-4-methoxy-6-tert-butylphenoxy)methoxymethane (yield: 91%, boiling point: 125°–130° C. (1 mmHg), IR: 3480, 3390, 1630, 1600 cm$^{-1}$).

Reference Example 2

(1) To a mixed solution comprising 8.6 g of 2,4-dimethoxyphenol and 80 ml of carbon disulfide ($CS_2$) was added dropwise 2.86 ml of bromine at 10° to 15° C. After stirring the mixture at room temperature for one hour, water was added to the reaction mixture and the reaction mixture was extracted with diethyl ether. The extract was washed and dried, and the solvent was removed under reduced pressure. Hexane was added to the obtained residue and the precipitated crystals were collected by filtration to give 12.0 g of 3-bromo-4,6-dimethoxyphenol (yield: 92%, melting point: 78°–80° C.).

(2) A mixed solution of 12 g of the product thus obtained and 20 ml of dimethylformamide (DMF) was added dropwise to a suspension of 100 ml of DMF containing 2.5 g of 60% sodium hydride under ice-cooling. After stirring the mixture at room temperature for 30 minutes, 4.7 ml of methoxymethyl chloride was added dropwise to the mixture and the resulting mixture was stirred at room temperature for 17 hours. DMF was removed from the reaction mixture and water was added to the residue. The mixture was extracted with diethyl ether. The extract was washed and dried, and the solvent was removed under reduced pressure. The residue was applied to silica gel column chromatography (solvent; hexane:ethyl acetate=4:1) to give 14 g of (3-bromo-4,6-dimethoxyphenoxy)methoxymethane as oily product.

(3) A tetrahydrofuran (THF) solution (100 ml) of the oily product thus obtained was cooled to −78° C., 24.2 ml of 2.5M n-butyl lithium-hexane solution was added to the solution and the mixture was stirred at the same temperature for 45 minutes. To the mixture was added dropwise a mixed solution of 10 g of tosyl azide and 20 ml of THF at the same temperature, and the mixture was further stirred for 3 hours. To the mixture was added 170 ml of 0.3M aqueous sodium pyrophosphate ($Na_4P_2O_7$) solution. The resulting mixture was stirred at 0° to 5° C. for 2 hours and then at room temperature overnight. Insoluble materials were removed from the mixture by filtration and the filtrate was extracted with diethyl ether. The extract was washed and dried, and the solvent was removed under reduced pressure. The residue was applied to silica gel column chromatography (solvent; hexane:ethyl acetate=4:1) to give 9.1 g of (3-azido-4,6-dimethoxyphenoxy)methoxymethane.

(4) The product thus obtained was dissolved in 100 ml of tetrahydrofuran (THF), and under ice-cooling, 114 ml of 1M lithium aluminum hydride-diethyl ether solution was added dropwise to the solution. After stirring the mixture at the same temperature for 2 hours, 4.3 ml of water, 4.3 ml of a 15% aqueous sodium hydroxide solution and 12.9 ml of water were successively added dropwise to the mixture. After removing insoluble materials by filtration, the filtrate was extracted with ethyl acetate, and the extract was washed and dried. The solvent was removed from the extract under reduced pressure and the residue was purified by silica gel column chromatography (solvent; hexane:ethyl acetate=1:1) to give 5.8 g of (3-amino-4,6-dimethoxyphenoxy) methoxymethane (yield: 53%, oily product, IR: 3450, 3350 $cm^{-1}$).

Reference Example 3

(1) Conc. sulfuric acid (0.4 ml) was added to a mixed solution comprising 3.3 g of 2,4-dimethoxybenzaldehyde and 30 ml of methanol, and under ice-cooling, 2.93 ml of 30% hydrogen peroxide aqueous solution was added to the mixture. After stirring at room temperature for 4 hours, a 5% aqueous potassium hydrogen sulfite solution was added to the mixture and the solvent was removed under reduced pressure. The residue was extracted with diethyl ether, the extract was washed and dried and the solvent was removed under reduced pressure. The residue was purified by silica gel column chromatography (solvent; hexane:ethyl acetate= 4:1) to give 2.1 g of 2,4-dimethoxyphenol (yield: 69%, state: colorless oily product).

(2) The product (3.1 g) thus obtained was treated in the same manner as described in Reference example 1 (2) to give 3.6 g of 2,4-dimethoxyphenoxymethoxymethane (yield: 90%, colorless oily product).

(3) A mixed solution of 3.6 g of the product thus obtained and 50 ml of tetrahydrofuran (THF) was cooled to −78° C., and 21.6 ml of a 2M sec-butyl lithium-cyclohexane solution was added dropwise to the mixture. The mixture was further stirred for one hour. A mixed solution of 3.6 g of tosyl azide and 10 ml of THF was added dropwise to the mixture and the resulting mixture was stirred for 2 hours. The mixture was poured into 60.5 ml of 0.3M aqueous sodium pyrophosphate ($Na_4P_2O_7$) solution, and the resulting mixture was stirred under ice-cooling for 3 hours. The reaction mixture was extracted with diethyl ether. The extract was washed and dried and the solvent was removed under reduced pressure. The residue was applied to short silica gel column chromatography (solvent; hexane:ethyl acetate= 4:1). The eluate was condensed and the residue was dissolved in 30 ml of THF. Under ice-cooling, 29 ml of 1M lithium aluminum hydride-diethyl ether solution was added dropwise to the solution. After stirring the mixture at the same temperature for 2 hours, 1.1 ml of water, 1.1 ml of a 15% sodium hydroxide aqueous solution and 3.3 ml of water were successively added dropwise to the mixture. After removing insoluble materials by filtration, diethyl ether was added to the filtrate and the mixture was dried, and the solvent was removed under reduced pressure. The residue was purified by silica gel column chromatography (solvent; hexane:ethyl acetate=4:1) to give 1.25 g of (2-amino-4,6-dimethoxyphenoxy)methoxymethane (yield: 32%, oily product).

Reference Example 4

(1) To a mixed solution of 25 g of 3-methoxyphenol and 100 ml of carbon disulfide ($CS_2$) was added dropwise 10.3 ml of bromine at room temperature. After stirring the mixture for 30 minutes, the solvent was removed under reduced pressure, and water was added to the residue. The reaction mixture was extracted with diethyl ether. The extract was washed and dried, and the solvent was removed under reduced pressure to give 34.8 g of 2-bromo-5-methoxyphenol (yield: 85%, boiling point: 96°–98° C. (4 mmHg), colorless oily product).

(2) The product (20.3 g) thus obtained was added to a suspension of 100 ml of dimethylformamide (DMF) arid 4.3 g of 62% sodium hydride, and the mixture was stirred at room temperature for 30 minutes. Then, 20 ml of octyl bromide was added to the mixture and the mixture was further stirred at room temperature for 3 days. DMF was removed from the reaction mixture under reduced pressure, and water was added to the residue. The mixture was extracted with diethyl ether. The extract was washed and dried, and the solvent was removed under reduced pressure. The residue was evaporated under reduced pressure to give 25.3 g of 2-octyloxy-4-methoxy-bromobenzene (yield: 80%, boiling point: 160°–165° C. (3 mmHg), colorless oily product).

(3) A mixed solution of 25.3 g of the product thus obtained and 100 ml of tetrahydrofuran (THF) was cooled to −50° C. or lower. 38.5 ml of 2.5M n-butyl lithium-hexane solution was added to the solution and the mixture was stirred at the same temperature for 45 minutes. To the mixture was added dropwise a mixed solution of 7.45 ml of dimethylformamide (DMF) and 10 ml of THF, and the mixture was stirred at the same temperature for 10 minutes. Then, 10% acetic acid was added to the mixture and the solvent was removed under reduced pressure. The residue was extracted with diethyl ether. The extract was washed and dried, and the solvent was removed under reduced pressure. The residue was purified by silica gel column chromatography (solvent; hexane:ethyl acetate=9:1) to give 15.8 g of 2-octyloxy-4-methoxybenzaldehyde (yield: 74%, melting point: 37°–39° C.).

(4) The product (19.8 g) thus obtained was treated in the same manner as described in Reference example 3 (1) to give 17.1 g of 2-octyloxy-4-methoxyphenol (yield: 90%, melting point: 36°–38° C.).

(5) The product (10 g) thus obtained was treated in the same manner as described in Reference example 1 (2) to give 10.5 g of (2-octyloxy-4-methoxyphenoxy) methoxymethane (yield: 89%, colorless oily product).

(6) The product (10.5 g) thus obtained was treated in the same manner as described in Reference example 3 (3) to give 4.0 g of (2-amino-6-octyloxy-4-methoxyphenoxy) methoxymethane (yield: 36%, melting point: 59°–61°0C.).

Reference Example 5

Corresponding starting compound was treated in the same manner as described in Reference example 4 to give (2-amino-6-tetradecyloxy-4-methoxyphenoxy)methoxymethane (melting point: 66°–67° C.).

Reference Example 6

(1) A mixed solution of 15.2 g of 2-methoxy-4-formylphenol, 26 ml of diisopropyl ethylamine, 9 ml of methoxymethyl chloride and 100 ml of tetrahydrofuran (THF) was stirred at room temperature for 3.5 hours. The solvent was removed under reduced pressure. Water was added to the residue and the mixture was extracted with ethyl acetate. The extract was washed and dried, and the solvent was removed under reduced pressure. The residue was purified by silica gel column chromatography (solvent; hexane:ethyl acetate=4:1) to give 18.9 g of (4-formyl-2-methoxyphenoxy)methoxymethane (yield: 96%, melting point: 34°–37° C.).

(2) A mixture of 18.9 g of the product thus obtained, 25 g of 3-chloroperbenzoic acid (mCPBA) and 500 ml of dichloromethane was stirred under heating for 8 hours. After cooling, the reaction mixture was washed and dried. The solvent was removed under reduced pressure and the obtained residue was dissolved in 200 ml of methanol. 30 ml of an aqueous solution containing 6.5 g of 85% potassium hydroxide was added dropwise to the solution. The mixture was extracted with ethyl acetate. The extract was washed and dried and the solvent was removed under reduced pressure. The residue was purified by silica gel column chromatography (solvent; hexane:ethyl acetate=4:1) to give 13 g of (4-hydroxy-2-methoxyphenoxy)methoxymethane (yield: 73%, melting point: 70°–72° C.).

(3) The product (6.5 g) thus obtained was treated in the same manner as described in Reference example 4 (2), and the obtained residue was purified by silica gel column chromatography (solvent; hexane:ethyl acetate=4:1) to give 9.6 g of (4-octyloxy-2-methoxyphenoxy)methoxymethane (yield: 92%, colorless oily product).

(4) The product (9.6 g) thus obtained was treated in the same manner as described in Reference example 3 (3) to give 6.7 g of (2-amino-4-octyloxy-6-methoxyphenoxy)methoxymethane (yield: 66%, melting point: 56°–57° C.).

Reference Example 7

Corresponding starting compound was treated in the same manner as described in Reference example 6 to give (2-amino-4-hexadecyloxy-6-methoxyphenoxy)methoxymethane (IR: 3450, 3350 cm$^{-1}$).

Reference Example 8

(1) 4-Methoxyphenol (124.14 g) was treated in the same manner as described in Reference example 4 (1) to give 161 g of 2-bromo-4-methoxyphenol (yield: 79%, melting point: 37°–38° C.).

(2) After treating 48.93 g of the product thus obtained in the same manner as described in Reference example 1 (2), the resulting material was evaporated under reduced pressure to give 50.583 g of (2-bromo-4-methoxyphenoxy)methoxymethane (yield: 85%, boiling point: 100° C. (2 mmHg), colorless oily product). methoxymethane(3) A mixed solution of 12.1 g of the product thus obtained and 60 ml of THF was cooled to −60° to −50° C., and 20.5 ml of 2.5M n-butyl lithium-hexane solution was added dropwise to the solution. The mixture was stirred at the same temperature for 30 minutes, and 14.088 g of octyl iodide was added dropwise to the mixture. After stirring the mixture at room temperature overnight, water was added to the reaction mixture and the mixture was extracted with diethyl ether. The extract was washed, dried and condensed, and then evaporated under reduced pressure to give 8.238 g of (4-methoxy-2-octylphenoxy)methoxymethane (yield: 60%, boiling point: 155°–160° C. (2 mmHg), colorless oily product).

(4) To a mixed solution of 8.238 g of the product thus obtained and 73 ml of THF was added dropwise at −60° to −70° C. 42.6 ml of 0.76M sec-butyl lithium-cyclohexane solution. After stirring the mixture at the same temperature for 1.5 hours, 8.09 g of diphenylphosphoryl azide (DPPA) was added dropwise and the mixture was further stirred for 2 hours. At the same temperature, 36.2 ml of a 70% sodium bis(2-methoxyethoxy)aluminum hydride-toluene solution was added dropwise to the mixture and the resulting mixture was stirred at 0° C. for one hour and then at room temperature for 30 minutes. Ice water was added to the reaction mixture and insoluble materials were removed by filtration from the mixture. The filtrate was extracted with diethyl ether. The extract was washed and dried, and the solvent was removed under reduced pressure. The residue was purified by silica gel column chromatography (solvent; hexane:ethyl acetate=4:1) to give 5.07 g of (2-amino-4-methoxy-6-octylphenoxy)methoxymethane (yield: 58%, oily product, IR: 3450, 3350, 1605 cm$^{-1}$).

Reference Examples 9 to 11

Corresponding starting materials were treated in the same manner as described in Reference example 8 to give the following compounds.

(Reference Example 9)

(2-Amino-4-methoxy-6-methylphenoxy)methoxymethane oily product

NMR (δ ppm, CDCl$_3$): 2.20 (3H, s), 3.55 (3H, s), 3.67 (3H, s), 3.83 (2H, s), 4.90 (2H, s), 6.12 (2H, s)

(Reference Example 10)

(2-Amino-4-methoxy-6-ethylphenoxy)methoxymethane oily product

NMR (δ ppm, CDCl$_3$): 1.20 (3H, t), 2.60 (2H, q), 3.60 (3H, s), 3.73 (3H, s), 3.92 (2H, br.s), 4.93 (2H, s), 6.16 (2H, s)

(Reference Example 11)

(2-Amino-4-methoxy-6-tetradecylphenoxy)methoxymethane melting point: 46°–48° C.

Reference Example 12

(1) A mixture of 19.85 g of tert-butylhydroquinone, 10.7 ml of ethyl bromide and 200 ml of dimethylformamide (DMF) was cooled to −78° C., and 4.82 g of 62.5% sodium hydride was added to the mixture. The temperature of the mixture was raised to 0° C., and the mixture was further stirred under ice-cooling for 30 minutes. The reaction mixture was poured into ice water, and the mixture was extracted with ethyl acetate. The extract was washed and dried, and the solvent was removed under reduced pressure. The residue was purified by silica gel column chromatography (solvent; hexane:ethyl acetate=10:1), and recrystallized from hexane to give 5.045 g of 4-ethoxy-2-tert-butylphenol (yield: 22%, melting point: 96°–98° C.).

(2) The product (3.328 g) thus obtained was treated in the same manner as described in Reference example 1 (1) to give 7.118 g of 2-(4-methoxyphenylazo)-4-ethoxy-6-tert-butylphenol (yield: 84%, melting point: 105°–108° C.).

(3) The product (7.06 g) thus obtained was treated in the same manner as described in Reference example 1 (2) and then the resulting material was purified by silica gel column chromatography (solvent; hexane:ethyl acetate=10:1) to give 7.315 g of [2-(4-methoxyphenylazo)-4-ethoxy-6-tert-butylphenoxy]methoxymethane (yield: 91%, brown oily product, IR: 1600 cm$^{-1}$).

(4) To a mixed solution of 7.31 g of the product thus obtained and 73 ml of methanol was added 1 g of 10% palladium-carbon (Pd-C). The mixture was subjected to catalytic reduction at normal temperature under normal pressure for one hour. After removing the catalyst by filtration, the filtrate was condensed under reduced pressure and the residue was purified by silica gel column chromatography (solvent; hexane:ethyl acetate=4:1) to give 4.51 g of (2-amino-4-ethoxy-6-tert-butylphenoxy)-methoxymethane (yield: 91%, oily product, IR: 3464, 3373, 1615, 1593 cm$^{-1}$).

Reference Examples 13 and 14

Corresponding starting materials were treated in the same manner as described in Reference example 12 to give the following compounds.

(Reference Example 13)

(2-Amino-6-tert-butyl-4-hexyloxyphenoxy) methoxymethane oily product IR: 3466, 3374, 1594 cm$^{-1}$ (Reference Example 14)

(2-Amino-6-tert-butyl-4-isopropyloxyphenoxy) methoxymethane oily product IR: 3464, 3373, 1591 cm.$^{-1}$ Reference Example 15

A mixture of 21.057 g of N,N-dimethyl-p-phenylenediamine, 18.2 ml of cycloheptanone and 100 ml of toluene was refluxed for 4 hours by using a Dean-Stark's apparatus. The solvent was removed under reduced pressure, and the residue was dissolved in 200 ml of methanol. To the solution was added 2 g of 10% palladium-carbon (Pd-C), and the mixture was subjected to catalytic reduction by using a Parr's reduction apparatus at room temperature for 3 hours. After removing the catalyst by filtration, the filtrate was condensed and the residue was purified by silica gel column chromatography (solvent; hexane:ethyl acetate=3:2) to give 29.478 g of N-4-dimethylaminophenyl-N-cycloheptylamine (yield: 82%, brown oily product, IR (film): 3375, 2926, 1517 cm$^{-1}$).

Reference Examples 16 to 48

Corresponding starting materials are treated in the same manner as described in Reference example 15 to give the compounds as shown in Table 25.

TABLE 25

$$\begin{array}{c} R^5 \\ | \\ HN-R^6 \end{array}$$

| Reference example | —R$^5$ | —R$^6$ | State |
|---|---|---|---|
| 16 | —CH$_2$—phenyl | cyclohexyl | Oily product |
| 17 | —CH$_2$—(2,3,4-trimethoxyphenyl) (OMe, OMe, OMe) | cyclohexyl | Oily product |
| 18 | —CH$_2$—(pyridyl, N) | cyclohexyl | Oily product |
| 19 | —CH$_2$—(benzo[1,3]dioxol-yl, O-CH$_2$-O) | cyclohexyl | Oily product |
| 20 | —CH$_2$—(pyridyl, N) | cyclohexyl | Oily product |

TABLE 25-continued $$\begin{array}{c} R^5 \\ | \\ HN-R^6 \end{array}$$

| Reference example | —R⁵ | —R⁶ | State |
|---|---|---|---|
| 21 | —CH₂-(2-pyridyl) | cyclohexyl | Oily product |
| 22 | —CH₂-phenyl | 4-(NHCOC(CH₃)₃)-cyclohexyl | Oily product |
| 23 | —CH₂-phenyl | —CH₂-cyclohexyl | Oily product |
| 24 | 4-NMe₂-phenyl | —CH₂-cyclohexyl | Oily product |
| 25 | —CH₂-phenyl | cycloheptyl | Oily product |
| 26 | —CH₂-phenyl | cyclopentyl | Oily product |
| 27 | 4-NMe₂-phenyl | cyclopentyl | Oily product |
| 28 | 4-NMe₂-phenyl | cyclooctyl | Oily product |
| 29 | cycloheptyl | 4-(NH-cycloheptyl)-cyclohexyl | Oily product |
| 30 | cycloheptyl | 4-(NHC(O)OC(CH₃)₃)-phenyl | Oily product |
| 31 | cycloheptyl | 3-pyridyl | Oily product |

TABLE 25-continued
$$\text{HN}\overset{\text{R}^5}{-}\text{R}^6$$
| Reference example | —R⁵ | —R⁶ | State |
|---|---|---|---|
| 32 | 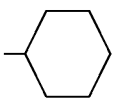 | 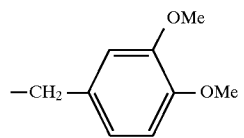 —CH₂—C₆H₃(OMe)₂ (3,4-dimethoxybenzyl) | Oily product |
| 33 | 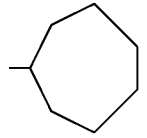 | 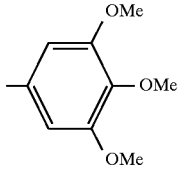 —C₆H₂(OMe)₃ (3,4,5-trimethoxyphenyl) | Oily product |
| 34 | 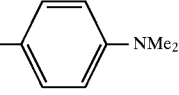 4-NMe₂-C₆H₄— | 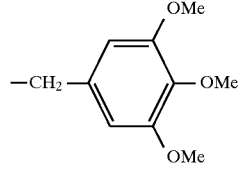 —CH₂—C₆H₂(OMe)₃ | Oily product |
| 35 |  | 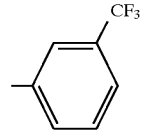 3-CF₃-C₆H₄— | Oily product |
| 36 |  | 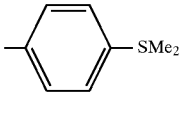 4-SMe₂-C₆H₄— | Oily product |
| 37 |  | 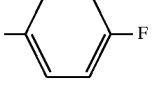 4-F-C₆H₄— | Oily product |
| 38 | 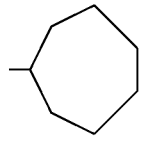 | 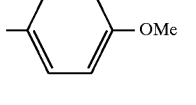 4-OMe-C₆H₄— | Oily product |
| 39 | 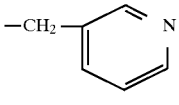 —CH₂-(3-pyridyl) | 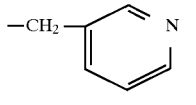 —CH₂-(3-pyridyl) | Oily product |
| 40 | 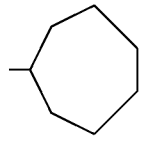 | —(CH₂)₃NMe₂ | Oily product |

TABLE 25-continued $$\begin{array}{c} R^5 \\ | \\ HN-R^6 \end{array}$$

| Reference example | −R⁵ | −R⁶ | State |
|---|---|---|---|
| 41 | cycloheptyl | 3-NMe₂-phenyl | Oily product |
| 42 | −(CH₂)₃−N(morpholino) | −CH₂-pyridyl | Oily product |
| 43 | −(CH₂)₂NMe₂ | −CH₂-pyridyl | Oily product |
| 44 | −(CH₂)₂-(N-methylpyrrolidinyl) | −CH₂-pyridyl | Oily product |
| 45 | −CH₂-pyridyl | pyridyl | Oily product |
| 46 | pyridyl | −CH₂-pyridyl | Oily product |
| 47 | pyridyl | −CH₂-pyridyl | Oily product |
| 48 | −CH₂-phenyl | −CH₂-piperidinyl (NH) | Oily product |

Reference Example 49

Under ice-cooling, to 30 ml of a THF solution containing 13.7 g of 1,4-diaminocyclohexane was added dropwise 30 ml of a THF solution containing 8.73 g of di-tert-butyl dicarbonate. The mixture was stirred at the same temperature for 30 minutes and further at room temperature overnight. Then, THF was removed under reduced pressure and a saturated saline solution was added to the residue. The mixture was extracted with ethyl acetate. The extract was washed and dried, and the solvent was removed to give 4.3 g of 1-tert-butoxycarbonylamino-4-aminocyclohexane (yield: 50%, oily product, IR (KBr): 3343, 1683, 1525 cm⁻¹).

Reference Example 50 p-Phenylenediamine was treated in the same manner as described in Reference example 49 to give N-tert-butoxycarbonyl-p-phenylenediamine (melting point: 115°–116° C.).

Reference Example 51

A mixture of 3.50 g of N,N-dimethyl-p-phenylenediamine, 4.592 g of heptanal, 9.095 g of triacetoxyborohydride, 1.841 g of acetic acid and 257 ml of dichloromethane was stirred at room temperature for one hour. A saturated sodium hydrogen carbonate solution is added to the mixture, and the mixture was extracted with ethyl acetate. The extract was washed and dried, and the solvent was removed under reduced pressure. The residue obtained was purified by silica gel column chromatography (solvent; hexane:ethyl acetate=2:1) to give 2.819 g of N,N-dimethyl-N'-heptyl-p-phenylenediamine (yield: 39%, oily product, IR (film): 3375, 2927, 1519 cm⁻¹).

Reference Example 52

N-benzyloxycarbonyl-4-aminocyclohexanone and aniline were treated in the same manner as described in Reference example 51 to give N-benzyloxycarbonyl-N'-phenyl-1,4-diaminocyclohexane.

Reference Example 53

(1) Benzyloxycarbonyl chloride (12.4 ml) was added dropwise to a mixture of 10 g of trans-4-aminocyclohexanol, 13.3 ml of triethylamine and 300 ml of dichloromethane under ice-cooling, and the mixture was stirred at room temperature for one hour. The reaction mixture was washed and dried, and the solvent was removed under reduced pressure. The residue was recrystallized from an ethyl acetate solution to give 5.80 g of N-benzyloxycarbonyl-trans-4-aminocyclohexanol (yield: 27%, melting point: 148°–151° C.).

(2) To 1000 ml of dichloromethane suspension containing 25.9 g of pyridinium chlorochromate (PCC) was added dropwise under ice-cooling a mixture of 15 g of N-benzyloxycarbonyl-trans-4-aminocyclohexanol and 1000 ml of dichloromethane. The resulting mixture was stirred at room temperature for 4 hours. Then, diethyl ether was added to the reaction mixture and insoluble materials were removed by filtration from the mixture. The filtrate was condensed and the residue was purified by silica gel column chromatography (solvent; chloroform:methanol=10:1) to give 10.562 g of N-benzyloxycarbonyl-4-aminocyclohexanone (yield: 71%, melting point: 65°–69° C.).

Reference Example 54

Tetrabromomethane (19.4 g) was added to a mixture of 5.0 g of 2-cyclohexylethanol, 12.28 g of triphenylphosphine and 400 ml of dichloromethane, and the mixture was stirred at room temperature for 5 minutes. The mixture was washed and dried, and the solvent was removed under reduced pressure. The residue was applied to short silica gel column chromatography (solvent; hexane). A condensed eluate was dissolved in 50 ml of hexamethylphosphoramide (HMPA), and 5.31 g of N,N-dimethyl-p-phenylenediamine and 5.39 g of potassium carbonate were added to the solution. The resulting mixture was stirred at room temperature overnight. A saturated saline solution was added to the reaction mixture and the mixture was extracted with ethyl acetate. The extract was washed and dried, and the solvent was removed under reduced pressure. The residue was purified by silica gel column chromatography (solvent; chloroform:ethyl acetate= 2:1) to give 3.205 g of N'-(2-cyclohexylethyl)-N,N-dimethyl-p-phenylenediamine (yield: 33%, brown oily product, IR (film): 3350, 1519 $cm^{-1}$).

Reference Examples 55 and 56

Corresponding starting materials are treated in the same manner as described in Reference example 54 to give the compounds shown in Table 26.

TABLE 26

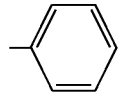

Reference Example 57

Under ice-cooling, 1.87 g of 62% sodium hydride was added to 100 ml of a dimethylformamide (DMF) solution containing 10.00 g of N-benzyloxycarbonylaniline, and the mixture was stirred at room temperature for one hour. Under ice-cooling, to the above mixture was added dropwise 50 ml of a DMF solution containing 10.31 g of ethyl 6-bromohexanoate, and the resulting mixture was stirred at room temperature overnight. DMF was removed under reduced pressure and water was added to the residue. The mixture was extracted with ethyl acetate. The extract was washed and dried, and the solvent was removed under reduced pressure. The residue was dissolved in 160 ml of methanol and 2 g of 10% palladium-carbon (Pd-C) was added to the solution. The mixture was subjected to catalytic reduction at normal temperature under normal pressure for 2 hours. After removing the catalyst by filtration, the filtrate was condensed and the residue was purified by silica gel column chromatography (solvent; hexane:ethyl acetate=4:1) to give 8.13 g of N-ethoxycarbonylpentyl-N-phenylamine (yield; 79%, melting point: 34°–37° C.).

Reference Examples 58 to 76

Corresponding starting materials are treated in the same manner as described in Reference example 57 to give the compounds as shown in Table 27.

TABLE 27

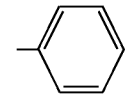

TABLE 27-continued $$\begin{array}{c} R^5 \\ | \\ HN-R^6 \end{array}$$

| Reference example | —R⁵ | —R⁶ | Melting point (°C.), etc. |
|---|---|---|---|
| 59 | 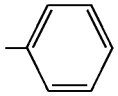 | —(CH₂)₄COOEt | Powder |
| 60 | 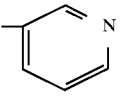 | —(CH₂)₅COOEt | Oily product |
| 61 | 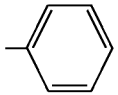 | —(CH₂)₃COOEt | Oily product |
| 62 | 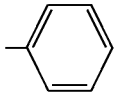 | —(CH₂)₆COOEt | Oily product |
| 63 | —CH₂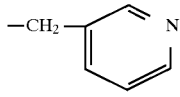 | —(CH₂)₅COOEt | Oily product |
| 64 | 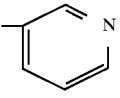 | —(CH₂)₄COOEt | Oily product |
| 65 | 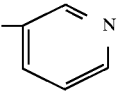 | —(CH₂)₆COOEt | Oily product |
| 66 | 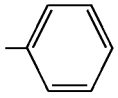 | —(CH₂)₂COOEt | Oily product |
| 67 | —(CH₂)₁₅CH₃ | 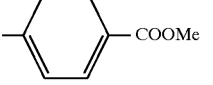—COOMe | 94–95 |
| 68 | 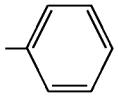 | —CH₂COOEt | Oily product |
| 69 | 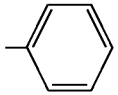 | —(CH₂)₅CH₃ | Oily product |
| 70 | —(CH₂)₇CH₃ | 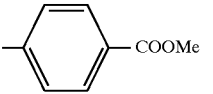—COOMe | Oily product |
| 71 | —(CH₂)₁₃CH₃ | 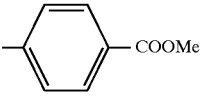—COOMe | Oily product |

TABLE 27-continued $$\underset{HN-R^6}{\overset{R^5}{|}}$$

| Reference example | —R⁵ | —R⁶ | Melting point (°C.), etc. |
|---|---|---|---|
| 72 | 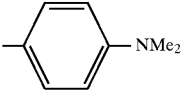 —NMe₂ | —(CH₂)₇CH₃ | Oily product |
| 73 | 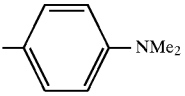 —NMe₂ | —CH₂COOEt | Oily product |
| 74 | 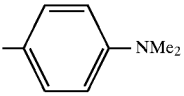 —NMe₂ | —CH₂— | Dihydrochloride Oily product |
| 75 | 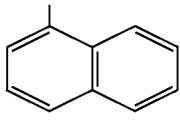 | —(CH₂)₃COOEt | Oily product |
| 76 | 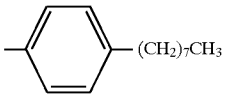 —(CH₂)₇CH₃ | —CH₂COOEt | Oily product |

Reference Example 77

A mixture of 10.0 g of 4-octylaniline, 8.6 g of bromocyclo-heptane, 13.5 g of potassium carbonate and 50 ml of hexamethylphosphoramide (HMPA) was stirred at 90° to 100° C. for 7 hours. After cooling, a saturated saline solution was added to the reaction mixture and the mixture was extracted with ethyl acetate. The extract was washed and dried, and the solvent was removed under reduced pressure. The residue was purified by silica gel column chromatography (solvent; hexane:ethyl acetate=50:1) to give 7.79 g of N-cycloheptyl-N-(4-octylphenyl)amine (yield: 53%, brown oily product, IR (film): 3390, 2925, 2854, 1617, 1518 cm⁻¹).

Reference Examples 78 to 92

Corresponding starting materials are treated in the same manner as described in Reference example 77 to give the compounds as shown in Table 28.

TABLE 28

$$\underset{HN-R^6}{\overset{R^5}{|}}$$

| Reference example | —R⁵ | —R⁶ | Melting point (°C.), etc. |
|---|---|---|---|
| 78 | 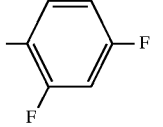 | —(CH₂)₃COOEt | Oily product |
| 79 | 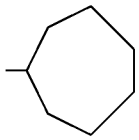 | —(CH₂)₃COOEt | Hydrobromide salt 196–199 |

TABLE 28-continued $$\begin{array}{c} R^5 \\ | \\ HN-R^6 \end{array}$$

| Reference example | —R⁵ | —R⁶ | Melting point (°C.), etc. |
|---|---|---|---|
| 80 | 4-NMe₂-C₆H₄— | —(CH₂)₃COOEt | Oily product |
| 81 | cyclohexyl | —(CH₂)₃COOEt | Hydrobromide salt 137–139 |
| 82 | 4-(CH₂)₇CH₃-C₆H₄— | —(CH₂)₃COOEt | Oily product |
| 83 | CH(Ph)₂ | —(CH₂)₃COOEt | Oily product |
| 84 | phenyl | —CH₂-cyclohexyl | Oily product |
| 85 | 4-NMe₂-C₆H₄— | cyclohexyl | Oily product |
| 86 | 4-NMe₂-C₆H₄— | —CH(Ph)₂ | 85–88 |
| 87 | —CH₂-(4-pyridyl) | —CH₂-(4-pyridyl) | Oily product |
| 88 | —CH₂-(2-pyridyl) | —CH₂-(2-pyridyl) | Oily product |
| 89 | —CH₂-(3-pyridyl) | —CH₂-(2-pyridyl) | Oily product |
| 90 | —CH₂-(4-pyridyl) | —CH₂-(3-pyridyl) | Oily product |
| 91 | —CH₂-(4-pyridyl) | —CH₂-(2-pyridyl) | Oily product |
| 92 | —CH₂-phenyl | —(CH₂)₃COOEt | Oily product |

Reference Example 93

(1) A mixture of 6.92 g of N-benzyloxycarbonyl-2-iodo-ethylamine, 4.00 g of 1-benzylpiperazine, 15.66 g of potassium carbonate and 40 ml of hexamethylphosphoramide (HMPA) was stirred at room temperature for overnight. Water was added to the reaction mixture, and the resulting mixture was extracted with diethyl ether. The extract was washed and dried, and the solvent was removed under reduced pressure. The residue was purified by silica gel column chromatography (solvent; chloroform:methanol= 15:1) to give 5.63 g of N-benzyloxycarbonyl-2-(4-benzylpiperazin-1-yl)ethylamine (yield: 70%, oily product, IR: 3230, 2910, 1710 cm$^{-}$).

(2) To the product (2.29 g) thus obtained was added a 30% hydrogen bromide-acetic acid solution, and the mixture was stirred at room temperature for one hour. Diethyl ether was added to the reaction mixture and the resulting crystals were collected by filtration. To the crystals were added an aqueous saturated sodium hydrogen carbonate solution, the mixture was extracted with chloroform, and the chloroform layer was washed and dried. By removing the solvent from the chloroform layer, 1.18 g of 2-(4-benzylpiperazin-1-yl)ethylamine (yield: 83%, oily product, IR: 3350, 2930, 2850, 2800 cm$^{-1}$).

Reference Examples 94 to 99

Corresponding starting materials are treated in the same manner as described in Reference example 93 to give the compounds as shown in Table 29.

TABLE 29

$H_2N-R^6$

| Reference example | $-R^6$ | Melting point (°C.), etc. |
|---|---|---|
| 94 | $-(CH_2)_2\text{-}NH\text{-}CH(Ph)(Ph)$ | Oily product |
| 95 | $-(CH_2)_2\text{-}N\text{(piperazine)}N\text{-}CH(Ph)(Ph)$ | Oily product |
| 96 | $-(CH_2)_3\text{-}N\text{(piperazine)}N\text{-}CH(Ph)(Ph)$ | Trihydrochloride >200 |
| 97 | $-(CH_2)_3N(CH_2)_2\text{-}(2,5\text{-dimethoxyphenyl})$, with $CH_3$ on N | Oily product |
| 98 | $-(CH_2)_2\text{-}N\text{(piperidinylidene)}=C(Ph)(Ph)$ | Oily product |

TABLE 29-continued $H_2N-R^6$

| Reference example | $-R^6$ | Melting point (°C.), etc. |
|---|---|---|
| 99 | $-(CH_2)_2\text{-}N\text{(piperidinylidene)}=C(4\text{-F-Ph})(4\text{-F-Ph})$ | Oily product |

Reference Example 100

(1) A mixture of 3.7 g of N-(tert-butoxycarbonyl)piperazine, 2.5 g of bromodiphenylmethane, 6.9 g of potassium carbonate and 20 ml of hexamethylphosphoramide was stirred at 40° to 50° C. for 4 hours. After cooling, water was added and the reaction mixture was extracted with diethyl ether. The exact was washed and dried, and the solvent was removed under reduced pressure. Hexane was added to the precipitated crystals and the crystals were collected by filtration to give 2.5 g of 4-(tert-butoxycarbonyl)-1-diphenylmethylpiperazine (melting point: 129°–131° C.).

(2) The product (5.0 g) thus obtained was dissolved in 20 ml of 26% hydrogen chloide-dioxane solution, and the mixture was stirred at room temperature for 30 minutes. The solvent was removed from the reaction mixture under reduced pressure. An aqueous 10% potassium carbonate solution was added to the residue and the mixture was extracted with ethyl acetate. The extract was washed and dried, the solvent was removed under reduced pressure. Hexane was added to the precipitated crystals and the crystals were collected by filtration to give 3.1 g of 1-diphenylmethylpiperazine (melting point: 73°–75° C.).

Reference Example 101

(1) A mixture of 25 g of 2-(4-hydroxyphenyl)ethylamine hydrochloride, 36 g of sodium hydrogen carbonate, 200 ml of water and 200 ml of ethyl acetate was ice-cooled. 24.6 g of benzyloxycarbonyl chloride was added dropwise to the mixture. After stirring the mixture at room temperature for 20 hours, the organic layer was separated and washed, and the solvent was removed from the organic layer under reduced pressure. The residue was crystallized from a hexane solution to give 31 g of N-benzyloxycarbonylamino-2-(4-hydroxyphenyl)ethylamine (yield: 79%, melting point: 94°–97° C.).

(2) A mixture of 9.5 g of 3-chloropropanol, 37 ml of dibutylamine and 50 ml of dimethylsulfoxide was stirred at 70°–80° C. for 8 hours. After cooling, water was added to the mixture and the mixture was extracted with ethyl acetate. The extract was washed and dried, and the solvent was removed from the mixture under reduced pressure. The residue was dissolved in 50 ml of chloroform, and under ice-cooling, 8 ml of thionyl chloride was added dropwise to the solution. After stirring at 50° C. for 3 hours, the solvent was removed from the reaction mixture under reduced pressure. Water was added to the residue and the mixture was washed with diethyl ether. The mixture was made alkaline with potassium carbonate and extracted with ethyl acetate. The extract was washed and dried, and the solvent was removed from the extract under reduced pressure. The residue was purified by silica gel column chromatography (solvent; chloroform:ethanol=20:1) to give 12 g of N,N-dibutyl-3-chloropropylamine (yield: 58%, oily product).

NMR (δ ppm, CDCl$_3$): 0.91 (6H, s), 1.2–1.5 (8H, m), 1.88 (2H, q), 2.34–2.41 (4H, m), 2.53 (2H, t), 3.60 (2H, t)

(3) Under ice-cooling, to 20 ml of a dimethylformamide (DMF) suspension containing 850 mg of 62% sodium hydride was added little by little 5.4 g of N-benzyloxycarbonylamino-2-(4-hydroxyphenyl) ethylamine, and the mixture was stirred at room temperature for 20 minutes. Then, the mixture was ice-cooled, 10 ml of a DMF solution containing 4.5 g of N,N-dibutyl-3-chloropropylamine was added thereto. Further, after stirring the mixture at room temperature for 24 hours, water was added thereto and the mixture was extracted with diethyl ether. The extract was washed and dried, and the solvent was removed from the extract under reduced pressure. The residue was purified by silica gel column chromatography (solvent; hexane:ethyl acetate=2:1 and then chloroform:ethanol=20:1) to give 5.5 g of N-benzyloxycarbonyl-2-[4-(3-dibutylaminopropyloxy) phenyl]ethylamine (yield: 63%, oily product, IR (film): 3310, 1710 cm$^{-1}$).

(4) Conc. hydrochloric acid (2.1 ml) and g of 10% palladium-carbon (Pd-C) were added to 100 ml of an ethanol solution containing 5.4 g of N-benzyloxycarbonyl-2-[4-(3-dibutylaminopropyloxy)phenyl]ethylamine. The mixture was subjected to catalytic reduction at normal temperature under normal pressure for 1.5 hours. After removing the catalyst by filtration, the filtrate was condensed and the residue was dissolved in water. The aqueous solution was washed with diethyl ether and made alkaline with potassium carbonate, and the mixture was extracted with ethyl acetate. The extract was washed and dried, and the solvent was removed under reduced pressure to give 3.2 g of 2-[4-(3-dibutylaminopropyloxy)phenyl]ethylamine (yield: 85%, oily product).

NMR (δ ppm, CDCl$_3$): 0.89 (6H, t), 1.2–1.5 (8H, m), 1.58 (2H, br.s), 1.90 (2H, q), 2.42 (4H, t), 2.59 (2H, t), 2.68 (2H, t), 2.92 (2H, t), 3.98 (2H, t), 6.81–7.11 (4H, m)

Reference Example 102

Corresponding starting material is treated in the same manner as described in Reference example 101 to give the compound as shown in Table 30.

TABLE 30

H$_2$N—R$^6$

| Reference example | —R$^6$ | Melting point (°C.), etc. |
|---|---|---|
| 102 | 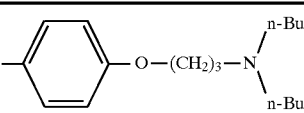 | Oily product |

Reference Example 103

Under ice-cooling, to 100 ml of a methanol solution containing 3.875 g of N-(4-piperidylmethyl)-N-benzylamine was added dropwise a mixed solution of 4.139 g of di-tert-butyl dicarbonate ((Boc)$_2$O) and 20 ml of methanol. After stirring the mixture at the same temperature for 30 minutes, methanol was removed from the reaction mixture under reduced pressure and the residue was purified by silica gel column chromatography (solvent; chloroform:methanol=19:1) to give 2.72 g of N-(1-tert-butoxycarbonyl-piperidin-4-ylmethyl)-N-benzylamine (yield: 47%, IR (film): 1693 cm$^{-1}$).

Reference Example 104

Under ice-cooling, to 200 ml of a tetrahydrofuran (THF) solution containing 5.0 g of N-(4-piperidylmethyl)-N-benzylamine was added dropwise 50 ml of a THF solution containing 2.9 ml of benzyl bromide. After stirring the mixture at the same temperature for one hour, THF was removed from the reaction mixture under reduced pressure and a saturated sodium hydrogen carbonate aqueous solution was added to the residue. The mixture was extracted with ethyl acetate. The extract was washed and dried, and the solvent was removed under reduced pressure. Precipitated crystals were recrystallized from an ethanol solution to give 3.6 g of N-(1-benzylpiperidin-4-ylmethyl)-N-benzylamine (yield: 50%, melting point: 240° C. or higher).

Reference Example 105

Under ice-cooling, 3.46 g of benzyloxycarbonyl chloride was added dropwise to a mixed solution of 4.15 g of N-(4-piperidylmethyl)-N-benzylamine, 2.10 g of triethylamine and 200 ml of THF. After stirring the mixture at the same temperature for 3 hours and then at room temperature for 2 hours, water was added to the mixture and the mixture was extracted with ethyl acetate. The extract was washed and dried, and the solvent was removed under reduced pressure. The obtained residue was purified by silica gel column chromatography (solvent; chloroform:methanol=19:1) to give 3.41 g of N-(1-benzyloxycarbonylpiperidin-4-ylmethyl)-N-benzylamine (yield: 50%, IR: 1702 cm$^{-1}$).

Reference Example 106

4-Piperidylmethylamine and 3-formylpyridine were treated in the same manner as described in Reference example 2 to give N-(4-piperidylmethyl)-N-(3-pyridylmethyl)amine.

The product thus obtained and di-tert-butyl dicarbonate ((Boc)$_2$O) were treated in the same manner as described in Reference example 103 to give N-(1-tert-butoxycarbonylpiperidin-4-ylmethyl)-N-(3-pyridylmethyl) amine (IR: 3320, 1688 cm$^{-1}$).

Reference Example 107

Under ice-cooling, 10 drops of a 50% choline solution was added to a mixture of 20.0 g of 3-(trifluoromethyl) phenylhydrazine and 6.63 g of acrylonitrile, and the mixture was heated at 95° C. for one hour. After allowed to stand for cooling, 22 ml of 1N hydrochloric acid was added and the mixture was stirred at 95° C. for 10 minutes. After subjecting the mixture to hot activated charcoal treatment, the mixture was adjusted to an alkaline pH with a 10% aqueous sodium hydroxide solution under ice-cooling. Precipitated crystals were collected by filtration and washed, and recrystallized from a mixed solution of hexane and ethyl acetate to give 17.27 g of 1-[3-(trifluoromethyl)phenyl]-3-amino-2-pyrazoline (yield: 66%, melting point: 104°–107° C.).

Reference Example 108

(1) A mixed solution of 20 g of 1,2,3-trimethoxybenzene and 100 ml of tetrahydrofuran (THF) was cooled to −78° C., and 140 ml of a hexane solution containing 1M sec-butyl lithium (sec-BuLi) was added dropwise thereto. After stirring the mixture at the same temperature for 45 minutes, 11 ml of dimethylformamide (DMF) was added to the reaction mixture. The mixture was stirred at −50° C. or lower for 45 minutes. Then, a 10% acetic acid aqueous solution was added to the mixture, and the resulting mixture was extracted with diethyl ether. The extract was washed and dried, and the solvent was removed under reduced pressure. The residue was purified by silica gel column chromatography (solvent; hexane:ethyl acetate=9:1) to give 5.7 g of 2,3,4-trimethoxybenzaldehyde (yield: 24%, oily product).

(2) The product thus obtained was treated in the same manner as described in Reference example 3 to give (2-amino-4,5,6-trimethoxyphenoxy)methoxymethane (oily product).

NMR (δ ppm, $CDCl_3$): 3.57 (3H, s), 3.75 (3H, s), 3.77 (3H, s), 3.88 (3H, s), 3.6–3.8 (2H, br.s), 5.03 (2H, s), 6.08 (1H, s)

The phenol compound (1) or pharmaceutically acceptable salts thereof of the present invention have excellent inhibitory effects on lipid peroxidation, foam cell formation of macrophages, oxidized LDL formation, ACAT activity, mouse anti-oxidative action, reperfusion-induced arrhythmia, brain edema, carbon tetrachloride-induced hepatopathy and the like so that they are effective for the prevention and the treatment of ischemic diseases (cardiac infarction, cerebral infarction, reperfusion disorder, etc.), atherosclerosis, inflammation, hepatopathy and the like. Also, the desired compounds of the present invention have less toxicity and thus they are used as a medical compound in high safety.

We claim:

1. A phenol compound represented by the formula (1):

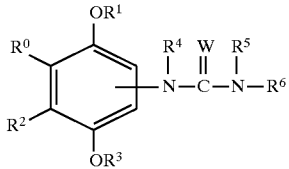

(1)

wherein $R^0$ represents a hydrogen atom, an alkyl group, a substituted alkyl group, an alkyloxy group, or a substituted alkyloxy group; $R^1$ represents an alkyl group or a substituted alkyl group; $R^2$ represents an alkyl group, substituted alkyl group, an alkyloxy group, or a substituted alkyloxy group; $OR^3$ represents a hydroxyl group or a hydroxyl group which is protected by an acyl group, a lower alkyloxy-lower alkyl group, a lower alkyloxycarbonyl group, a lower alkylcarbonyloxy-lower alkyl group or an aralkyl group; $R^4$ represents a hydrogen atom, a lower alkyl group, a substituted lower alkyl group, an acyl group, or a substituted acyl group; W represents O, S or $NR^7$, wherein $R^7$ represents a hydrogen atom, an alkyl group, an aryl group, a hydroxyl group or an alkyloxy group; a group of the formula (2):

(2)

which represents a mono- or di-substituted amino group or a nitrogen-containing heterocyclic group, or a pharmaceutically acceptable salt thereof.

2. The compound according to claim 1, wherein $R^5$ and $R^6$ each may be the same or different and represents a hydrogen atom, an alkyl group, a substituted alkyl group, an alkenyl group, substituted alkenyl group, an aryl group, substituted aryl group, an amino group, a substituted amino group, or a heterocyclic group.

3. The compound according to claim 2, wherein $R^5$ and $R^6$ may be the same or different, and each represents (1) an alkyl group or an alkyl group substituted by at least one substituent selected from the group consisting of an alkyl group, a halogenated alkyl group, a carboxyalkyl group, an alkyloxycarbonylalkyl group, a hydroxyalkyl group, a dihydroxyalkyl group, a trihydroxyalkyl group, an N-alkylaminoalkyl group, an N,N-dialkylaminoalkyl group, an N-(diphenylalkyl)aminoalkyl group, a carbamoylalkyl group, an N-alkylcarbamoylalkyl group, an N,N-dialkylcarbamoylalkyl group, an N-(dihydroxyalkyl) carbamoylalkyl group, a morpholinocarbonylalkyl group, a heterocyclic group-substituted alkyl group, a cycloalkyl group, a cycloalkylalkyl group, an arylalkyl group and a diarylalkyl group;

(2) an amino group or an amino group substituted by at least one substituent selected from the group consisting of an amino group, a monoalkylamino group, a dialkylamino group, an arylamino group, an arylsulfonylamino group and an arylcarbamoylamino group;

(3) an alkenyl group or an alkenyl group substituted by an alkyl group;

(4) an aryl group or an aryl group substituted by at least one substituent selected from the group consisting of a phenyl group, an aminophenyl group, an N-alkylaminophenyl group and an N,N-dialkylaminophenyl group; or (5) a saturated or unsaturated 3 to 12-membered monocyclic or dicyclic heterocyclic group having a hetero atom selected from sulfur atom, oxygen atom and nitrogen atom.

4. The compound according to claim 3, wherein said heterocyclic group is a 5 to 10-membered monocyclic or dicyclic heterocyclic group or a 5 to 10-membered monocylic or dicyclic heterocyclic group which is mono-, di- or tri-substituted by 1 to 3 substituents selected from the group consisting of hydroxyl group, a hydroxyalkyl group, an alkyloxy group, an alkyloxycarbonyl group, an alkylcarbonyl group, an alkyl group, a cycloalkyl group, a cycloalkylalkyl group, a pyridylalkyl group, oxo group, carboxyl group, phenyl group, a phenylalkyl group, a diphenylalkyl group, phenylpiperazinyl group, a phenylalkyloxycarbonyl group, N-phenylcarbamoyl group and an N-phenylcarbamoylaminoalkyl group.

5. The compound according to claim 4, wherein said heterocyclic group is a heterocyclic group selected from the group consisting of pyridyl group, pyridinio group, piperazinyl group, piperidyl group, pyrazolinyl group, imidazolyl group, imidazolidinyl group, pyrrolidinyl group, morpholinyl group, pyradinyl group, benzimidazolyl group, quinolyl group and tetrahydroquinolyl group.

6. The compound according to claim 1, wherein $R^5$ and $R^6$ form a saturated or unsaturated 3 to 12-membered monocyclic or dicyclic nitrogen-containing heterocyclic group.

7. The compound according to claim 6, wherein said nitrogen-containing heterocyclic group is a 5 to 10-membered monocyclic or dicyclic heterocyclic group or a 5 to 10-membered monocyclic or dicyclic heterocyclic group which is mono-, di- or tri-substituted by 1 to 3 substituents selected from the group consisting of a halogen atom, an alkyl group, hydroxyl group, a hydroxyalkyl group, an alkyloxy group, oxo group, carboxyl group, an alkyloxycarbonyl group, a phenylalkylaminoalkyl group, phenyl group, a halogenophenyl group, an aminophenyl group, a nitrophenyl group, an aminophenylalkenyl group, an aminoalkyl group, an aminophenylalkyl group, an N,N-diaminoalkylaminophenylalkyl group, an N-arylureiodoalkyl group, a morpholinylphenylalkyl group, a pyridylalkyl group, a benzimidazolylalkyl group, a hydroxyphenyl group, a diaminophenyl group, an N-alkylaminophenyl group, an N,N-dialkylaminophenyl group, an amidinophenyl group, a piperadinophenyl group, a morpholinophenyl group, pyrrolidinyl group, piperidyl group, indolyl group, pyrimidinyl group, benzimidazolyl group and pyridyl group.

8. The compound according to claim 7, wherein the heterocyclic group is selected from piperazinyl group, piperidino group, piperidyl group, morpholino group, morpholinyl group, pyrrolidinyl group, thiomorpholinyl group, dihydroquinolyl group, tetrahydroquinolyl group and imidazolydinyl group.

9. The compound according to claim 3, wherein $R^0$ is hydrogen atom, $R^1$ is an alkyl group, $R^2$ is an alkyl group, $OR^3$ is hydroxyl group, $R^4$ is hydrogen atom and W is oxygen atom.

10. A compound selected from
2-[3-(3-pyridylmethyl)ureido]-4-methoxy-6-tert-butylphenol,
2-(3-cyclohexyl-3-phenylmethylureido)-4-methoxy-6-tert-butylphenol,
2-[3-cycloheptyl-3-(4-dimethylaminophenyl)ureido]-4-methoxy-6-tert-butylphenol,
2-[3,3-di(pyridylmethyl)ureido]-4-methoxy-6-tert-butylphenol,
2-[4-(4-aminophenyl)piperazin-1-yl]amido-4-methoxy-6-tert-butylphenol,
2-[3-(2-cyclohexylethyl)-3-(4-dimethylaminophenyl)ureido]-4-methoxy-6-tert-butylphenol, and
2-[3-(4-pyridylmethyl)-3-(3-pyridyl)ureido]-4-methoxy-6-tert-butylphenol.

11. A process for preparing a compound (1) according to claim 1 or a pharmaceutically acceptable salt thereof which comprises the steps of A) reacting a compound represented by the formula (c):

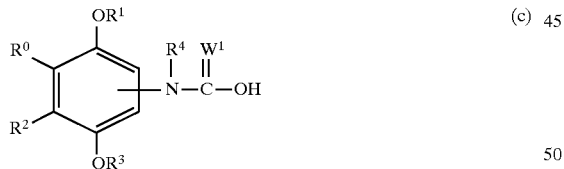

or a reactive derivative thereof selected from the group consisting of a corresponding acid halide, mixed acid anhydride and active ester, wherein $R^0$, $R^1$, $R^2$, $R^3$ and $R^4$ have the same meanings as defined in claim 1; and $W^1$ represents an oxygen atom or a sulfur atom, with a compound represented by the formula (b):

wherein $NR^5R^6$ represents an amino group which is mono- or di-substituted, or a heterocyclic group containing a nitrogen atom, or a salt thereof to form a compound represented by the formula (1-a):

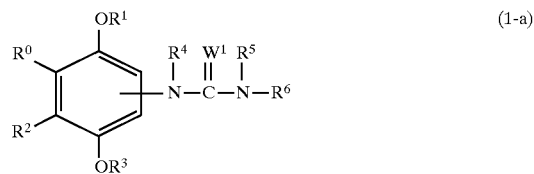

wherein the respective symbols have the same meanings as defined above; or

B) reacting a compound represented by the formula (d):

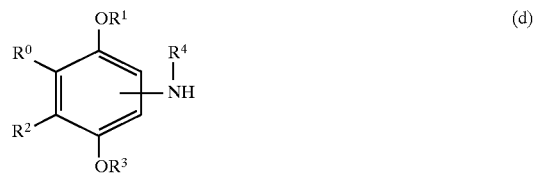

wherein the respective symbols have the same meanings as defined in claim 1,
or a salt thereof with an active ester of a compound represented by the formula (e):

wherein the respective symbols have the same meanings as defined in claim 1,
to form a compound represented by the formula (1-b):

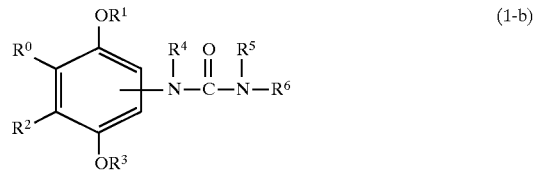

wherein the respective symbols have the same meanings as defined above; or

C) reacting the compound of the above formula (d) with a compound represented by the formula (f):

wherein $R^{51}$ represents a hydrogen atom, an alkyl group, substituted alkyl group, an alkenyl group, a substituted alkenyl group, an aryl group, a substituted aryl group, an amino group, a substituted amino group, or a heterocyclic group, and the other symbol has the same meaning as defined above,
to form a compound represented by the formula (1-c):

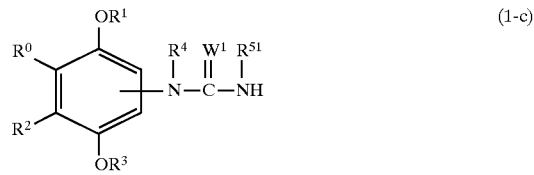

wherein the respective symbols have the same meanings as defined above; and,

D) when the $W^1$ of the product represented by the formula (1-a) or (1-c) is sulfur atom, reacting the product (1-a) or (1-c) with a compound represented by the formula (g):

wherein R⁷ represents a hydrogen atom, an alkyl group, an aryl group, hydroxyl group or an alkyloxy group, to form a compound of the formula (1-d):

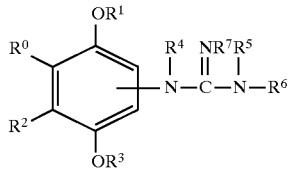

wherein the respective symbols have the same meanings as defined above,

E) and optionally formulating the product into a pharmaceutically acceptable salt thereof.

12. The process according to claim 11, wherein when the group —NR⁵R⁶ in the product (1) is a group containing a protected carboxyl group, the process further comprises subjecting the product (1) to a deprotection reaction to convert the product to a corresponding compound (1) wherein the group —NR⁵R⁶ is a group containing a free carboxyl group.

13. The process according to claim 11, wherein when the group —NR⁵R⁶ in the product (1) is a group containing a free carboxyl group, the process further comprises reacting the product (1) with a compound of the formula (h):

wherein —NR⁸R⁹ represents a mono- or di-substituted amino group or a 5 to 10-membered nitrogen-containing heterocyclic group, to convert the product to a compound (1) wherein the group —NR⁵R⁶ is a group containing a corresponding amido group.

14. The process according to claim 11, wherein when the group —NR⁵R⁶ in the product (1) is an amino group or mono-substituted amino group, the process further comprises reacting the product (1) with an alkylating agent of the formula (i):

wherein R¹⁰ represents an alkyl group or a substituted alkyl group, and X represents a leaving group, to convert the product to a corresponding compound (1) wherein the group —NR⁵R⁶ is a monoalkyl-substituted or a dialkyl-substituted amino group.

15. The process according to claim 11, wherein, when the group OR³ of the product (1-a), (1-b), (1-c) or (1-d) is a protected hydroxyl group, removing the protecting group from the product prior to the formulation of the pharmaceutically acceptable salt thereof.

16. The process according to claim 11, wherein, when the group OR³ of the product (1-a), (1-b), (1-c) or (1-d) is a hydroxyl group, protecting the hydroxyl group prior to the formulation of the pharmaceutically acceptable salt thereof.

17. A phenol compound represented by the formula (1):

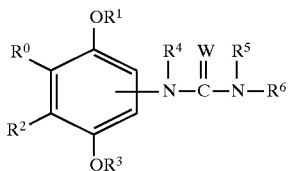

wherein R⁰ represents a hydrogen atom, an alkyl group, a substituted alkyl group, an alkyloxy group, or a substituted alkyloxy group; R¹ represents an alkyl group or a substituted alkyl group; R² represents an alkyl group, substituted alkyl group, an alkyloxy group, or a substituted alkyloxy group; OR³ represents a hydroxyl group or a hydroxyl group which is protected by an acyl group, a lower alkyloxy-lower alkyl group, a lower alkyloxycarbonyl group, a lower alkylcarbonyloxy-lower alkyl group or an aralkyl group; R⁴ represents a hydrogen atom, a lower alkyl group, a substituted lower alkyl group, an acyl group, or a substituted acyl group; W represents O, S or NR⁷, wherein R⁷ represents a hydrogen atom, an alkyl group, an aryl group, a hydroxyl group or an alkyloxy group; a group of the formula (2):

which represents a mono- or di-substituted amino group or monocyclic or dicyclic heterocyclic group or a 5 to 10-membered monocyclic or dicyclic heterocyclic group which is mono-, di- or tri-substituted by 1 to 3 substituents selected from the group consisting of a halogen atom, an alkyl group, hydroxyl group, a kydroxyalkyl group, an alkyloxy group, oxo group, carboxyl group, an alkyloxycarbonyl group, a phenylalkylaminoalkyl group, phenyl group, a halogenophenyl group, an aminophenyl group, a nitrophenyl group, an aminophenylalkenyl group, an aminoalkyl group, an aminophenylalkyl group, an N,N-diaminoalkylaminophenylalkyl group, an N-arylureidoalkyl group, a morpholinylphenylalkyl group, a pyridylalkyl group, a benzimidazolylalkyl group, a hydroxyphenyl group, a diaminophenyl group, an N-alkylaminophenyl group, an N,N-dialkylaminophenyl group, an amidinophenyl group, a piperadinophenyl group, a morpholinophenyl group, pyrrolidinyl group, piperidyl group, indolyl group, pyrimidinyl group, benzimidazolyl group and pyridyl group, or a pharmaceutically acceptable salt thereof.

18. A pharmaceutical composition, which comprises a therapeutically effective amount of the phenol compound as set forth in any one of claims 1 to 10, and a pharmaceutically acceptable carrier or diluent thereof.

19. A method for prophylaxis or treatment of atherosclerosis, cardiac infarction, cell damage or arrythmia at ischemia-reperfusion in a patient, which comprises administering to said patient a therapeutically effective amount of the phenol compound as set forth in any one of claims 1 to 10.

* * * * *